(12) United States Patent
Gurney et al.

(10) Patent No.: US 6,638,731 B2
(45) Date of Patent: Oct. 28, 2003

(54) HUMAN SEL-10 POLYPEPTIDES AND POLYNUCLEOTIDES THAT ENCODE THEM

(75) Inventors: Mark E. Gurney, Grand Rapids, MI (US); Adele M. Pauley, Plainwell, MI (US); Jinhe Li, Kalamazoo, MI (US)

(73) Assignee: Pharmacia and Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/213,888

(22) Filed: Dec. 17, 1998

(65) Prior Publication Data

US 2002/0164683 A1 Nov. 7, 2002

Related U.S. Application Data

(60) Provisional application No. 60/068,243, filed on Dec. 19, 1997.

(51) Int. Cl.$^7$ .......................... C12P 21/06; C12N 1/20; C12N 15/00; C07H 21/04

(52) U.S. Cl. ................ 435/69.1; 435/252.3; 435/320.1; 536/23.1

(58) Field of Search .......................... 435/325, 320.1, 435/252.3, 69.1; 536/23.1–23.5; 530/300, 350

(56) References Cited

FOREIGN PATENT DOCUMENTS

WO     WO 97/11956     4/1997     .......... C07H/21/04

OTHER PUBLICATIONS

Skolnick et al., Trends in Biotech., 18(1):34–39, 2000.*
Yochem et al., J. Mol. Biol., 195:233–45, 1987.*
Choh, PNAS 77(6):3211–14, 1980.*
Jenkins, PCR Methods and Appl., S77–82, 1994.*
Crooke, Antisesne & Nucl. Acid Drug Dev., 8:115–22, 1998.*
Genbank Accession No. AA625610; Oct. 15, 1997.*
Sambrook et al, Cold Spring Harbor Labs, 17.1–17.44, 1989.*
D.R. Borchelt, G. Thinakaran, C.B. Eckman, M.K. Lee, F. Davenport, T. Ratovitsky, C.–M. Prada, G. Kim, S. Seekins, D. Yager, H.H. Slunt, R. Wang, M. M. Seeger, A.I. Levey, S.E. Gandy, N.G. Copeland, N.A. Jenkins, D.L. Price, S.G. Younkin, S.S. Sisodia, "Familial Alzheimer's Disease–Linked Presenilin 1 Variants Elevate Aβ1–42/1–40 Ratio In Vitro and In Vivo," Neuron, 1996, 17:1005–1013.
D.R. Borchelt, T. Ratovitski, J. van Lare, M.K. Lee, V. Gonzales, N.A. Jenkins, N.G. Copeland, D.L. Price, S.S. Sisodia, "Accelerated Amyloid Deposition in the Brains of Transgenic Mice Coexpressing Mutant Presenilin 1 and Amyloid PrecursorProteins," Neuron, 1997, 19:939–945.

M. Citron, D. Westaway, W. Xia, G. Carlson, T. Diehl, G. Levesque, K. Johnson–Wood, M. Lee, P. Seubert, A. Davis, D. Kholodenko, R. Motter, R. Sherrington,l B. Perry, H. Yao, R. Strome, I. Lieberburg, J. Rommens, S. Kim, D. Schenk, P. Fraser, P. St. George Hyslop, D.J. Selkoe, "Mutant presenilins of Alzheimer's disease increase production of 42–residue amyloid β–protein in both transfected cells and transgenic mice," Nat. Med., 1997, 3:67–72.
A. Doan, G. Thinakaran, D.R. Borchelt, H.H. Slunt, T. Ratovitsky, M. Podlisny, D.J. Selkoe, M. Seeger, S.E. Gandy, D.L. Price, S.S. Sisodia, "Protein Topology of Presenilin 1," Neuron, 1996, 17:1023–1030.
K. Duff, C. Eckman, C. Zehr, X. Yu, C.–M. Prada, J. Perez–Tur, M. Hutton, L. Buee, Y. Harigaya, D. Yager, D. Morgan, M.N. Gordon, L. Holcomb, L. Refolo, B. Zenk, J. Hardy, S. Younkin, "Increased amyloid–β42(43) in brains of mice expressing mutant presenilin 1," Nature, 1996, 383:710–713.
I. Greenwald, G. Seydoux, "Analysis of gain–of–function mutations of the lin–12 gene of Caenorhabditis elegans," Nature, 1990, 346:197–9.
M. Hochstrasser, "Ubiquitin–dependent protein degradation," Annual Review of Genetics, 1996, 30:405–439.
E.J.A. Hubbard, G. Wu, J. Kitajewski, I. Greenwald, "sel–10, a negative regulator of lin–12 activity in Caenorhabditis elegans, encodes a member of the CDC4 family of proteins," Genes & Development, 1997, 11: 3182–3193.
T.W. Kim, W.H. Pettingell, O.G. Hallmark, R.D. Moir, W. Wasco, R.E. Tanzi, "Endoproteolytic Cleavage and Proteasomal Degradation of Presenilin 2 in Transfected Cells," Journal of Biological Chemistry, 1997, 272: 11006–11010.
D.M. Kovacs, H.J. Fausett, K.J. Page, T.–W. Kim, R.D. Moir, D.E.Merriam, R.D. Hollister, O.G. Hallmark, R. Mancini, K.M. Felsenstein, B.T. Hyman, R.E. Tanzi, W. Wasco, "Alzheimer–associated presenilins 1 and 2: Neronal expression in brain and localization to intracellular membranes in mammalian cells," Nat. Med., 1996, 2:224–229.
D. Levitan, T.G. Doyle, D. Brousseau, M.K. Lee, G. Thinakaran, H.H. Slunt, S.S. Sisodia, I. Greenwald, "Assessment of normal and mutant human presenilin function in Caenorhabditis elegans," Proc. Natl. Acad. Sci. USA, 1996, 93: 14940–4.
D. Levitan, I. Greenwald, "Facilitation of lin–12–mediated signalling by sel–12, a Caenorhabditis elegans S182 Alzheimer's disease gene," Nature, 1995, 377: 351–4.

(List continued on next page.)

Primary Examiner—Gary Kunz
Assistant Examiner—Sharon Turner
(74) Attorney, Agent, or Firm—Edward F. Rehberg; Lori Kerber

(57) ABSTRACT

The present invention provides isolated nucleic acid molecules comprising a polynucleotide encoding either of two alternative splice variants of human sel-10, one of which is expressed in hippocampal cells, and one of which is expressed in mammary cells. The invention also provides isolated sel-10 polypeptides and cell lines which express them in which Aβ processing is altered.

80 Claims, 2 Drawing Sheets

OTHER PUBLICATIONS

E. Levy–Lahad, W. Wasco, P. Poorkaj, D.M. Romano, J. Oshima, W.H. Pettingell, C.–E. Yu, P.D. Jondro, S.D. Schmidt, K. Wang, A.C. Crowley, Y.–H. Fu, S.Y. Guenette, D. Galas, E. Nemens, E.M. Wijsman, T.D. Bird, G.D. Schellenberg, R.E. Tanzi, "Candidate Gene for the Chromosome 1 Familial Alzheimer's Disease Locus," Science, 1995, 269: 973–977.

J. Li, J. Ma, H. Potter, "Identification and expression analysis of a potential familial Alzheimer disease gene on chromosome 1 related to AD3," Proc. Natl. Acad. Sci. U.S.A., 1995, 92:12180–12184.

M. Mercken, H. Takahashi, T. Honda, Z. Sato, M. Murayama, Y. Nakazato, K. Noguchi, K. Imahori, A. Takashima, "Characterization of human presenilin 1 using N–terminal specific monoclonal antibodies: Evidence that Alzheimer mutations affect proteolytic processing," FEBS Lett., 1996, 389:297–303.

M. Mullan, F. Crawford, K. Axelman, H. Houlden, L. Lilius, B. Winblad, L. Lannfelt, "A pathogenic mutation for probable Alzheimer's disease in the APP gene at the N–terminus of β–amyloid," Nat Genet, Aug. 1992, 1(5):345–7.

J. Perez–Tur, S. Froelich, G. Prihar, R. Crook, M. Baker, K. Duff, M. Wragg, F. Busfield, C. Lendon, R.F. Clark, P. Roques, R.A. Fuldner, J. Johnston, R. Cowburn, C. Forsell, K. Axelman, L. Lilius, H. Houlden, E. Karran, G.W. Roberts, M. Rossor, M.D. Adams, J. Hardy, A. Goate, L. Lannfelt, M. Hutton, "A Mutation in Alzheimer's disease destroying a splice acceptor site in the presenilin–1 gene," Neuroreport, 1995, 7:297–301.

E.I. Rogaev, R. Sherrington, E.A. Rogaeva, G. Levesque, M. Ikeda, Y. Liang, H. Chi, C. Lin, K. Holman, T. Tsuda, L. Mar, S. Sorbi, B. Nacmais, S. Piacentini, L. Amaducci, I. Chumakov, D. Cohen, L. Lannfelt, P.E. Fraser, J.M. Rommens, P.H. St George–Hyslop, "Familial Alzheimer's disease in kindreds with missense mutations in a gene on chromosome 1 related to the Alzheimer's disease type 3 gene," Nature, 1995, 376: 775–778.

D. Scheuner, C. Eckman, M. Jensen, X. Song, M. Citron, N. Suzukik, T.D. Bird, J. Hardy, M. Hutton, W. Kukull, E. Larson, E. Levy–Lahad, M. Viitanen, E. Peskind, P. Poorkaj, G. Schellenberg, R. Tanzi, W. Wasco, L. Lannfelt, D. Selkoe, S. Younkin, "Secreted amyloid β–protein similar to that in the senile plaques of Alzheimer's disease is increased in vivo by the presenilin 1 and 2 and APP mutations linked to familial Alzheimer's disease," Nat. Med., 1996, 2:864–870.

R. Sherrington, E.I. Rogaev, Y. Liang, E.A. Rogaeva, G. Levesque, M. Ikeda, H. Chi, C. Lin, G. Li, K. Holman, T. Tsuda, L. Mar, J.–F. Foncin, A.C. Bruni, M.P. Montesi, S. Sorbi, I. Rainero, L. Pinessi, L. Nee, I. Chumakov, D. Pollen, A. Brookes, P. Sanseau, R.J. Polinsky, W. Wasco, H.A.R. Da Silva, J.L. Haines, M.A. Pericak–Vance, R.E. Tanzi, A.D. Roses, P.E. Fraser, J.M. Rommens, P.H. St George–Hyslop, "Cloning of a gene bearing missense mutations in early–onset familial Alzheimer's disease," Nature, 1995, 375: 754–760.

M. Sundaram, I. Greenwald, "Genetic and Phenotypic Studies of Hypomorphic lin–12 Mutants in Caenorhabditis elegans," Genetics, 1993, 135: 755–763.

M. Sundaram, I. Greenwald, "Suppressors of a lin–12 Hypomorph Define Genes That Interact With Both lin–12 and glp–1 in Caenorhabditis elegans," Genetics, 1993, 135: 765–83.

Genbank H22962 Jul. 6, 1995.
Genbank H34371 Jul. 19, 1995.

* cited by examiner

SEQUENCE LISTING

<160> NUMBER OF SEQ ID NOS: 27

<210> SEQ ID NO 1
<211> LENGTH: 3550
<212> TYPE: DNA
<213> ORGANISM: Homo sapiens
<220> FEATURE:
<221> NAME/KEY: unsure
<222> LOCATION: (2485)
<220> FEATURE:
<221> NAME/KEY: unsure
<222> LOCATION: (3372)

<400> SEQUENCE: 1

```
ctcattattc cctcgagttc ttctcagtca agctgcatgt atgtatgtgt gtcccgagaa    60
gcggtttgat actgagctgc atttgccttt actgtggagt tttgttgccg gttctgctcc   120
ctaatcttcc ttttctgacg tgcctgagca tgtccacatt agaatctgtg acatacctac   180
ctgaaaaagg tttatattgt cagagactgc caagcagccg acacacgggg ggcacagaat   240
cactgaaggg gaaaaataca gaaaatatgg gtttctacgg cacattaaaa atgatttttt   300
acaaaatgaa aagaaagttg gaccatggtt ctgaggtccg ctcttttttct ttgggaaaga   360 aaccatgcaa agtctcagaa tatacaagta ccactgggct tgtaccatgt tcagcaacac   420
caacaacttt tggggacctc agagcagcca atggccaagg gcaacaacga cgccgaatta   480
catctgtcca gccacctaca ggcctccagg aatggctaaa aatgtttcag agctggagtg   540
gaccagagaa attgcttgct ttagatgaac tcattgatag ttgtgaacca acacaagtaa   600
aacatatgat gcaagtgata gaaccccagt ttcaacgaga cttcatttca ttgctcccta   660
aagagttggc actctatgtg ctttcattcc tggaacccaa agacctgcta caagcagctc   720
agacatgtcg ctactggaga attttggctg aagacaacct tctctggaga gagaaatgca   780
aagaagaggg gattgatgaa ccattgcaca tcaagagaag aaaagtaata aaaccaggtt   840
tcatacacag tccatggaaa agtgcataca tcagacagca cagaattgat actaactgga   900
ggcgaggaga actcaaatct cctaaggtgc tgaaaggaca tgatgatcat gtgatcacat   960
gcttacagtt ttgtggtaac cgaatagtta gtggttctga tgacaacact ttaaaagttt  1020
ggtcagcagt cacaggcaaa tgtctgagaa cattagtggg acatacaggt ggagtatggt  1080
catcacaaat gagagacaac atcatcatta gtggatctac agatcggaca ctcaaagtgt  1140
ggaatgcaga gactggagaa tgtatacaca cctatatgg gcatacttcc actgtgcgtt  1200
gtatgcatct tcatgaaaaa agagttgtta gcggttctcg agatgccact cttagggttt  1260
gggatattga gacaggccag tgtttacatg ttttgatggg tcatgttgca gcagtccgct  1320
gtgttcaata tgatggcagg agggttgtta gtggagcata tgattttatg gtaaaggtgt  1380
gggatccaga gactgaaacc tgtctacaca cgttgcaggg gcatactaat agagtctatt  1440
```

```
cattacagtt tgatggtatc catgtggtga gtggatctct tgatacatca atccgtgttt      1500
gggatgtgga gacagggaat tgcattcaca cgttaacagg gcaccagtcg ttaacaagtg      1560
gaatggaact caaagacaat attcttgtct ctgggaatgc agattctaca gttaaaatct      1620
gggatatcaa acaggacag tgtttacaaa cattgcaagg tcccaacaag catcagagtg      1680
ctgtgacctg tttacagttc aacaagaact tgtaattac cagctcagat gatggaactg       1740
taaaactatg ggacttgaaa acgggtgaat ttattcgaaa cctagtcaca ttggagagtg      1800
gggggagtgg gggagttgtg tggcggatca gagcctcaaa cacaaagctg gtgtgtgcag      1860
ttgggagtcg gaatgggact gaagaaacca agctgctggt gctggacttt gatgtggaca      1920
tgaagtgaag agcagaaaag atgaatttgt ccaattgtgt agacgatata ctccctgccc      1980
ttccccctgc aaaagaaaa aagaaaga aaagaaaaa aatcccttgt tctcagtggt          2040
gcaggatgtt ggcttggggc aacagattga aaagacctac agactaagaa ggaaaagaag      2100
aagagatgac aaaccataac tgacaagaga ggcgtctgct gtctcatcac ataaaaggct      2160
tcacttttga ctgagggcag ctttgcaaaa tgagactttc taaatcaaac caggtgcaat      2220
tatttcttta ttttcttctc cagtggtcat tggggcagtg ttaatgctga acatcatta       2280 cagattctgc tagcctgttc ttttaccact gacagctaga cacctagaaa ggaactgcaa      2340
taatatcaaa acaagtactg gttgactttc taattagaga gcatctgcaa caaaaagtca     2400
tttttctgga gtgaaaagc ttaaaaaaat tactgtgaat tgttttttgta cagttatcat     2460 gaaaagcttt tttttttatt ttttngccaa ccattgccaa tgtcaatcaa tcacagtatt     2520
agcctctgtt aatctattta ctgttgcttc catatacatt cttcaatgca tatgttgctc    2580
aaaggtggca agttgtcctg ggttctgtga gtcctgagat ggatttaatt cttgatgctg   2640
gtgctagaag taggtcttca aatatgggat tgttgtccca accctgtact gtactcccag    2700
tggccaaact tatttatgct gctaaatgaa agaaagaaaa aagcaaatta tttttttttat   2760 ttttttttctg ctgtgacgtt ttagtcccag actgaattcc aaatttgctc tagtttggtt    2820
atggaaaaaa gacttttttgc cactgaaact tgagccatct gtgcctctaa gaggctgaga    2880
atggaagagt ttcagataat aaagagtgaa gtttgcctgc aagtaaagaa ttgagagtgt    2940
gtgcaaagct tattttctt tatctgggca aaaattaaaa cacattcctt ggaacagagc      3000
tattacttgc ctgttctgtg gagaaacttt tcttttgag gctgtggtg aatggatgaa      3060 cgtacatcgt aaaactgaca aaatatttta aaaatatata aaacacaaaa ttaaaataaa     3120
gttgctggtc agtcttagtg ttttacagta tttgggaaaa caactgttac agttttattg    3180
ctctgagtaa ctgacaaagc agaaactatt cagttttgt agtaaaggcg tcacatgcaa      3240
acaaacaaaa tgaatgaaac agtcaaatgg tttgcctcat tctccaagag ccacaactca    3300
agctgaactg tgaaagtggt ttaacactgt atcctaggcg atctttttc ctccttctgt     3360 ttatttttt gnttgttta tttatagtct gatttaaaac aatcagattc aagttggtta     3420
attttagtta tgtaacaacc tgacatgatg gaggaaaaca acctttaaag ggattgtgtc    3480
tatggtttga ttcacttaga aatttttattt tcttataact taagtgcaat aaaatgtgtt    3540
ttttcatgtt                                                             3550
```

<210> SEQ ID NO 2
<211> LENGTH: 3571
<212> TYPE: DNA
<213> ORGANISM: Homo sapiens
<220> FEATURE:

```
<221> NAME/KEY: unsure
<222> LOCATION: (2506)
<220> FEATURE:
<221> NAME/KEY: unsure
<222> LOCATION: (3393)

<400> SEQUENCE: 2
```

| | | | | | |
|---|---|---|---|---|---|
| ctcagcaggt | caggacattt | ggtaggggaa | ggttgaaaga | caaaagcagc | aggccttggg | 60 |
| ttctcagcct | tttaaaaact | attattaaat | atatatttt | aaaatttagt | ggttagagct | 120 |
| tttagtaatg | tgcctgtatt | acatgtagag | agtattcgtc | aaccaagagg | agttttaaaa | 180 |
| tgtcaaaacc | gggaaaacct | actctaaacc | atggcttggt | tcctgttgat | cttaaaagtg | 240 |
| caaaagagcc | tctaccacat | caaaccgtga | tgaagatatt | tagcattagc | atcattgccc | 300 |
| aaggcctccc | tttttgtcga | agacggatga | aaagaaagtt | ggaccatggt | tctgaggtcc | 360 |
| gctcttttc | tttgggaaag | aaaccatgca | aagtctcaga | atatacaagt | accactgggc | 420 |
| ttgtaccatg | ttcagcaaca | ccaacaactt | tggggaccct | cagagcagcc | aatggccaag | 480 |
| ggcaacaacg | acgccgaatt | acatctgtcc | agccacctac | aggcctccag | gaatggctaa | 540 |
| aaatgtttca | gagctggagt | ggaccagaga | aattgcttgc | tttagatgaa | ctcattgata | 600 |
| gttgtgaacc | aacacaagta | aaacatatga | tgcaagtgat | agaaccccag | tttcaacgag | 660 |
| acttcatttc | attgctccct | aaagagttgg | cactctatgt | gctttcattc | ctggaaccca | 720 |
| aagacctgct | acaagcagct | cagacatgtc | gctactggag | aatttttggct | gaagacaacc | 780 |
| ttctctggag | agagaaatgc | aaagaagagg | ggattgatga | accattgcac | atcaagagaa | 840 |
| gaaaagtaat | aaaaccaggt | ttcatacaca | gtccatggaa | aagtgcatac | atcagacagc | 900 |
| acagaattga | tactaactgg | aggcgaggag | aactcaaatc | tcctaaggtg | ctgaaaggac | 960 |
| atgatgatca | tgtgatcaca | tgcttacagt | tttgtggtaa | ccgaatagtt | agtggttctg | 1020 |
| atgacaaacac | tttaaaagtt | tggtcagcag | tcacaggcaa | atgtctgaga | acattagtgg | 1080 |
| gacatacagg | tggagtatgg | tcatcacaaa | tgagagacaa | catcatcatt | agtggatcta | 1140 |
| cagatcggac | actcaaagtg | tggaatgcag | agactgagga | atgtatacac | accttatatg | 1200 |
| ggcatacttc | cactgtgcgt | tgtatgcatc | ttcatgaaaa | aagagttgtt | agcggttctc | 1260 |
| gagatgccac | tcttagggtt | tgggatattg | agacaggcca | gtgtttacat | gttttgatgg | 1320 |
| gtcatgttgc | agcagtccgc | tgtgttcaat | atgatggcag | gagggttgtt | agtggagcat | 1380 |
| atgatttat | ggtaaaggtg | tgggatccag | agactgaaac | ctgtctacac | acgttgcagg | 1440 |
| ggcatactaa | tagagtctat | tcattacagt | ttgatggtat | ccatgtggtg | agtggatctc | 1500 |
| ttgatacatc | aatccgtgtt | tgggatgtgg | agacagggaa | ttgcattcac | acgttaacag | 1560 |
| ggcaccagtc | gttaacaagt | ggaatggaac | tcaaagacaa | tattcttgtc | tctgggaatg | 1620 |
| cagattctac | agttaaaatc | tgggatatca | aacaggaca | gtgtttacaa | acattgcaag | 1680 |
| gtcccaacaa | gcatcagagt | gctgtgacct | gtttacagtt | caacaagaac | tttgtaatta | 1740 |
| ccagctcaga | tgatgaact | gtaaaactat | gggacttgaa | aacgggtgaa | tttattcgaa | 1800 |
| acctagtcac | attggagagt | ggggggagtg | ggggagttgt | gtggcggatc | agagcctcaa | 1860 |
| acacaaagct | ggtgtgtgca | gttgggagtc | ggaatgggac | tgaagaaacc | aagctgctgg | 1920 |
| tgctggactt | tgatgtggac | atgaagtgaa | gagcagaaaa | gatgaatttg | tccaattgtg | 1980 |
| tagacgatat | actccctgcc | cttcccctg | caaaaagaaa | aaagaaaag | aaaagaaaa | 2040 |
| aaatcccttg | ttctcagtgg | tgcaggatgt | tggcttgggg | caacagattg | aaaagaccta | 2100 |
| cagactaaga | aggaaaagaa | gaagagatga | caaaccataa | ctgacaagag | aggcgtctgc | 2160 |

```
tgtctcatca cataaaaggc ttcactttg  actgagggca gctttgcaaa atgagacttt   2220
ctaaatcaaa ccaggtgcaa ttatttcttt attttcttct ccagtggtca ttggggcagt   2280
gttaatgctg aaacatcatt acagattctg ctagcctgtt cttttaccac tgacagctag   2340
acacctagaa aggaactgca ataatatcaa aacaagtact ggttgacttt ctaattagag   2400
agcatctgca acaaaaagtc attttttctgg agtggaaaag cttaaaaaaa ttactgtgaa   2460
ttgtttttgt acagttatca tgaaaagctt ttttttttat tttttngcca accattgcca   2520
atgtcaatca atcacagtat tagcctctgt taatctattt actgttgctt ccatatacat   2580
tcttcaatgc atatgttgct caaggtggc  aagttgtcct gggttctgtg agtcctgaga   2640
tggatttaat tcttgatgct ggtgctagaa gtaggtcttc aaatatggga ttgttgtccc   2700
aaccctgtac tgtactccca gtggccaaac ttatttatgc tgctaaatga agaaagaaa    2760 aaagcaaatt atttttttta tttttttttct gctgtgacgt tttagtccca gactgaattc   2820
caaatttgct ctagttggt  tatggaaaaa agacttttg ccactgaaac ttgagccatc    2880
tgtgcctcta agaggctgag aatggaagag tttcagataa taaagagtga agtttgcctg    2940
caagtaaaga attgagagtg tgtgcaaagc ttatttctct ttatctgggc aaaaattaaa    3000
acacattcct tggaacagag ctattacttg cctgttctgt ggagaaactt tctttttga     3060 gggctgtggt gaatggatga acgtacatcg taaaactgac aaaatatttt aaaaatatat    3120
aaaacacaaa attaaaataa agttgctggt cagtcttagt gttttacagt atttgggaaa    3180
acaactgtta cagttttatt gctctgagta actgacaaag cagaaactat tcagtttttg    3240
tagtaaaggc gtcacatgca acaaacaaa  atgaatgaaa cagtcaaatg gtttgcctca    3300
ttctccaaga gccacaactc aagctgaact gtgaaagtgg tttaacactg tatcctaggc    3360
gatctttttt cctccttctg tttattttt  tgnttgtttt atttatagtc tgatttaaaa    3420
caatcagatt caagttggtt aattttagtt atgtaacaac ctgacatgat ggaggaaaac    3480 aaccttttaaa gggattgtgt ctatggtttg attcacttag aaattttatt ttcttataac   3540
ttaagtgcaa taaaatgtgt tttttcatgt t                                    3571
```

<210> SEQ ID NO 3
<211> LENGTH: 627
<212> TYPE: PRT
<213> ORGANISM: Homo sapiens

<400> SEQUENCE: 3

```
Met Cys Val Pro Arg Ser Gly Leu Ile Leu Ser Cys Ile Cys Leu Tyr
 1               5                  10                  15

Cys Gly Val Leu Leu Pro Val Leu Leu Pro Asn Leu Pro Phe Leu Thr
            20                  25                  30

Cys Leu Ser Met Ser Thr Leu Glu Ser Val Thr Tyr Leu Pro Glu Lys
        35                  40                  45

Gly Leu Tyr Cys Gln Arg Leu Pro Ser Ser Arg Thr His Gly Gly Thr
    50                  55                  60

Glu Ser Leu Lys Gly Lys Asn Thr Glu Asn Met Gly Phe Tyr Gly Thr
65                  70                  75                  80

Leu Lys Met Ile Phe Tyr Lys Met Lys Arg Lys Leu Asp His Gly Ser
                85                  90                  95

Glu Val Arg Ser Phe Ser Leu Gly Lys Lys Pro Cys Lys Val Ser Glu
            100                 105                 110

Tyr Thr Ser Thr Thr Gly Leu Val Pro Cys Ser Ala Thr Pro Thr Thr
```

-continued

```
                115                 120                 125
    Phe Gly Asp Leu Arg Ala Ala Asn Gly Gln Gly Gln Arg Arg
        130                 135                 140
Ile Thr Ser Val Gln Pro Pro Thr Gly Leu Gln Glu Trp Leu Lys Met
145                 150                 155                 160
Phe Gln Ser Trp Ser Gly Pro Glu Lys Leu Leu Ala Leu Asp Glu Leu
                165                 170                 175
Ile Asp Ser Cys Glu Pro Thr Gln Val Lys His Met Met Gln Val Ile
            180                 185                 190
Glu Pro Gln Phe Gln Arg Asp Phe Ile Ser Leu Leu Pro Lys Glu Leu
        195                 200                 205
Ala Leu Tyr Val Leu Ser Phe Leu Glu Pro Lys Asp Leu Leu Gln Ala
    210                 215                 220
Ala Gln Thr Cys Arg Tyr Trp Arg Ile Leu Ala Glu Asp Asn Leu Leu
225                 230                 235                 240
Trp Arg Glu Lys Cys Lys Glu Glu Gly Ile Asp Glu Pro Leu His Ile
                245                 250                 255
Lys Arg Arg Lys Val Ile Lys Pro Gly Phe Ile His Ser Pro Trp Lys
            260                 265                 270
Ser Ala Tyr Ile Arg Gln His Arg Ile Asp Thr Asn Trp Arg Arg Gly
        275                 280                 285
Glu Leu Lys Ser Pro Lys Val Leu Lys Gly His Asp Asp His Val Ile
    290                 295                 300
Thr Cys Leu Gln Phe Cys Gly Asn Arg Ile Val Ser Gly Ser Asp Asp
305                 310                 315                 320
Asn Thr Leu Lys Val Trp Ser Ala Val Thr Gly Lys Cys Leu Arg Thr
                325                 330                 335
Leu Val Gly His Thr Gly Gly Val Trp Ser Ser Gln Met Arg Asp Asn
            340                 345                 350
Ile Ile Ile Ser Gly Ser Thr Asp Arg Thr Leu Lys Val Trp Asn Ala
        355                 360                 365
Glu Thr Gly Glu Cys Ile His Thr Leu Tyr Gly His Thr Ser Thr Val
    370                 375                 380
Arg Cys Met His Leu His Glu Lys Arg Val Val Ser Gly Ser Arg Asp
385                 390                 395                 400
Ala Thr Leu Arg Val Trp Asp Ile Glu Thr Gly Gln Cys Leu His Val
                405                 410                 415
Leu Met Gly His Val Ala Ala Val Arg Cys Val Gln Tyr Asp Gly Arg
            420                 425                 430
Arg Val Val Ser Gly Ala Tyr Asp Phe Met Val Lys Val Trp Asp Pro
        435                 440                 445
Glu Thr Glu Thr Cys Leu His Thr Leu Gln Gly His Thr Asn Arg Val
    450                 455                 460
Tyr Ser Leu Gln Phe Asp Gly Ile His Val Val Ser Gly Ser Leu Asp
465                 470                 475                 480
Thr Ser Ile Arg Val Trp Asp Val Glu Thr Gly Asn Cys Ile His Thr
                485                 490                 495
Leu Thr Gly His Gln Ser Leu Thr Ser Gly Met Glu Leu Lys Asp Asn
            500                 505                 510
Ile Leu Val Ser Gly Asn Ala Asp Ser Thr Val Lys Ile Trp Asp Ile
        515                 520                 525
Lys Thr Gly Gln Cys Leu Gln Thr Leu Gln Gly Pro Asn Lys His Gln
    530                 535                 540
```

-continued

```
Ser Ala Val Thr Cys Leu Gln Phe Asn Lys Asn Phe Val Ile Thr Ser
545                 550                 555                 560

Ser Asp Asp Gly Thr Val Lys Leu Trp Asp Leu Lys Thr Gly Glu Phe
            565                 570                 575

Ile Arg Asn Leu Val Thr Leu Glu Ser Gly Ser Gly Val Val
            580                 585                 590

Trp Arg Ile Arg Ala Ser Asn Thr Lys Leu Val Cys Ala Val Gly Ser
        595                 600                 605

Arg Asn Gly Thr Glu Glu Thr Lys Leu Leu Val Leu Asp Phe Asp Val
        610                 615                 620

Asp Met Lys
625

<210> SEQ ID NO 4
<211> LENGTH: 592
<212> TYPE: PRT
<213> ORGANISM: Homo sapiens

<400> SEQUENCE: 4

Met Ser Thr Leu Glu Ser Val Thr Tyr Leu Pro Glu Lys Gly Leu Tyr
1               5                   10                  15

Cys Gln Arg Leu Pro Ser Ser Arg Thr His Gly Gly Thr Glu Ser Leu
            20                  25                  30

Lys Gly Lys Asn Thr Glu Asn Met Gly Phe Tyr Gly Thr Leu Lys Met
        35                  40                  45

Ile Phe Tyr Lys Met Lys Arg Lys Leu Asp His Gly Ser Glu Val Arg
    50                  55                  60

Ser Phe Ser Leu Gly Lys Lys Pro Cys Lys Val Ser Glu Tyr Thr Ser
65                  70                  75                  80

Thr Thr Gly Leu Val Pro Cys Ser Ala Thr Pro Thr Thr Phe Gly Asp
                85                  90                  95

Leu Arg Ala Ala Asn Gly Gln Gly Gln Gln Arg Arg Ile Thr Ser
            100                 105                 110

Val Gln Pro Pro Thr Gly Leu Gln Glu Trp Leu Lys Met Phe Gln Ser
        115                 120                 125

Trp Ser Gly Pro Glu Lys Leu Leu Ala Leu Asp Glu Leu Ile Asp Ser
    130                 135                 140

Cys Glu Pro Thr Gln Val Lys His Met Met Gln Val Ile Glu Pro Gln
145                 150                 155                 160

Phe Gln Arg Asp Phe Ile Ser Leu Leu Pro Lys Glu Leu Ala Leu Tyr
                165                 170                 175

Val Leu Ser Phe Leu Glu Pro Lys Asp Leu Leu Gln Ala Ala Gln Thr
            180                 185                 190

Cys Arg Tyr Trp Arg Ile Leu Ala Glu Asp Asn Leu Leu Trp Arg Glu
        195                 200                 205

Lys Cys Lys Glu Glu Gly Ile Asp Glu Pro Leu His Ile Lys Arg Arg
    210                 215                 220

Lys Val Ile Lys Pro Gly Phe Ile His Ser Pro Trp Lys Ser Ala Tyr
225                 230                 235                 240

Ile Arg Gln His Arg Ile Asp Thr Asn Trp Arg Arg Gly Glu Leu Lys
                245                 250                 255

Ser Pro Lys Val Leu Lys Gly His Asp Asp His Val Ile Thr Cys Leu
            260                 265                 270

Gln Phe Cys Gly Asn Arg Ile Val Ser Gly Ser Asp Asp Asn Thr Leu
```

-continued

```
            275                 280                 285
Lys Val Trp Ser Ala Val Thr Gly Lys Cys Leu Arg Thr Leu Val Gly
        290                 295                 300

His Thr Gly Gly Val Trp Ser Gln Met Arg Asp Asn Ile Ile Ile
305                 310                 315                 320

Ser Gly Ser Thr Asp Arg Thr Leu Lys Val Trp Asn Ala Glu Thr Gly
                325                 330                 335

Glu Cys Ile His Thr Leu Tyr Gly His Thr Ser Thr Val Arg Cys Met
                340                 345                 350

His Leu His Glu Lys Arg Val Val Ser Gly Ser Arg Asp Ala Thr Leu
            355                 360                 365

Arg Val Trp Asp Ile Glu Thr Gly Gln Cys Leu His Val Leu Met Gly
370                 375                 380

His Val Ala Ala Val Arg Cys Val Gln Tyr Asp Gly Arg Arg Val Val
385                 390                 395                 400

Ser Gly Ala Tyr Asp Phe Met Val Lys Val Trp Asp Pro Glu Thr Glu
                405                 410                 415

Thr Cys Leu His Thr Leu Gln Gly His Thr Asn Arg Val Tyr Ser Leu
                420                 425                 430

Gln Phe Asp Gly Ile His Val Val Ser Gly Ser Leu Asp Thr Ser Ile
            435                 440                 445

Arg Val Trp Asp Val Glu Thr Gly Asn Cys Ile His Thr Leu Thr Gly
450                 455                 460

His Gln Ser Leu Thr Ser Gly Met Glu Leu Lys Asp Asn Ile Leu Val
465                 470                 475                 480

Ser Gly Asn Ala Asp Ser Thr Val Lys Ile Trp Asp Ile Lys Thr Gly
                485                 490                 495

Gln Cys Leu Gln Thr Leu Gln Gly Pro Asn Lys His Gln Ser Ala Val
                500                 505                 510

Thr Cys Leu Gln Phe Asn Lys Asn Phe Val Ile Thr Ser Ser Asp Asp
            515                 520                 525

Gly Thr Val Lys Leu Trp Asp Leu Lys Thr Gly Glu Phe Ile Arg Asn
        530                 535                 540

Leu Val Thr Leu Glu Ser Gly Gly Ser Gly Gly Val Val Trp Arg Ile
545                 550                 555                 560

Arg Ala Ser Asn Thr Lys Leu Val Cys Ala Val Gly Ser Arg Asn Gly
                565                 570                 575

Thr Glu Glu Thr Lys Leu Leu Val Leu Asp Phe Asp Val Asp Met Lys
                580                 585                 590

<210> SEQ ID NO 5
<211> LENGTH: 553
<212> TYPE: PRT
<213> ORGANISM: Homo sapiens

<400> SEQUENCE: 5

Met Gly Phe Tyr Gly Thr Leu Lys Met Ile Phe Tyr Lys Met Lys Arg
1               5                   10                  15

Lys Leu Asp His Gly Ser Glu Val Arg Ser Phe Ser Leu Gly Lys Lys
            20                  25                  30

Pro Cys Lys Val Ser Glu Tyr Thr Ser Thr Thr Gly Leu Val Pro Cys
        35                  40                  45

Ser Ala Thr Pro Thr Thr Phe Gly Asp Leu Arg Ala Ala Asn Gly Gln
    50                  55                  60
```

```
Gly Gln Gln Arg Arg Arg Ile Thr Ser Val Gln Pro Pro Thr Gly Leu
 65                  70                  75                  80

Gln Glu Trp Leu Lys Met Phe Gln Ser Trp Ser Gly Pro Glu Lys Leu
                 85                  90                  95

Leu Ala Leu Asp Glu Leu Ile Asp Ser Cys Glu Pro Thr Gln Val Lys
                100                 105                 110

His Met Met Gln Val Ile Glu Pro Gln Phe Gln Arg Asp Phe Ile Ser
            115                 120                 125

Leu Leu Pro Lys Glu Leu Ala Leu Tyr Val Leu Ser Phe Leu Glu Pro
130                 135                 140

Lys Asp Leu Leu Gln Ala Ala Gln Thr Cys Arg Tyr Trp Arg Ile Leu
145                 150                 155                 160

Ala Glu Asp Asn Leu Leu Trp Arg Glu Lys Cys Lys Glu Glu Gly Ile
                165                 170                 175

Asp Glu Pro Leu His Ile Lys Arg Arg Lys Val Ile Lys Pro Gly Phe
            180                 185                 190

Ile His Ser Pro Trp Lys Ser Ala Tyr Ile Arg Gln His Arg Ile Asp
        195                 200                 205

Thr Asn Trp Arg Arg Gly Glu Leu Lys Ser Pro Lys Val Leu Lys Gly
    210                 215                 220

His Asp Asp His Val Ile Thr Cys Leu Gln Phe Cys Gly Asn Arg Ile
225                 230                 235                 240

Val Ser Gly Ser Asp Asp Asn Thr Leu Lys Val Trp Ser Ala Val Thr
                245                 250                 255

Gly Lys Cys Leu Arg Thr Leu Val Gly His Thr Gly Gly Val Trp Ser
            260                 265                 270

Ser Gln Met Arg Asp Asn Ile Ile Ile Ser Gly Ser Thr Asp Arg Thr
        275                 280                 285

Leu Lys Val Trp Asn Ala Glu Thr Gly Glu Cys Ile His Thr Leu Tyr
    290                 295                 300

Gly His Thr Ser Thr Val Arg Cys Met His Leu His Glu Lys Arg Val
305                 310                 315                 320

Val Ser Gly Ser Arg Asp Ala Thr Leu Arg Val Trp Asp Ile Glu Thr
                325                 330                 335

Gly Gln Cys Leu His Val Leu Met Gly His Val Ala Ala Val Arg Cys
            340                 345                 350

Val Gln Tyr Asp Gly Arg Arg Val Val Ser Gly Ala Tyr Asp Phe Met
        355                 360                 365

Val Lys Val Trp Asp Pro Glu Thr Glu Thr Cys Leu His Thr Leu Gln
    370                 375                 380

Gly His Thr Asn Arg Val Tyr Ser Leu Gln Phe Asp Gly Ile His Val
385                 390                 395                 400

Val Ser Gly Ser Leu Asp Thr Ser Ile Arg Val Trp Asp Val Glu Thr
                405                 410                 415

Gly Asn Cys Ile His Thr Leu Thr Gly His Gln Ser Leu Thr Ser Gly
            420                 425                 430

Met Glu Leu Lys Asp Asn Ile Leu Val Ser Gly Asn Ala Asp Ser Thr
        435                 440                 445

Val Lys Ile Trp Asp Ile Lys Thr Gly Gln Cys Leu Gln Thr Leu Gln
    450                 455                 460

Gly Pro Asn Lys His Gln Ser Ala Val Thr Cys Leu Gln Phe Asn Lys
465                 470                 475                 480

Asn Phe Val Ile Thr Ser Ser Asp Asp Gly Thr Val Lys Leu Trp Asp
```

-continued

```
                        485                 490                 495
Leu Lys Thr Gly Glu Phe Ile Arg Asn Leu Val Thr Leu Glu Ser Gly
                    500                 505                 510

Gly Ser Gly Gly Val Val Trp Arg Ile Arg Ala Ser Asn Thr Lys Leu
                515                 520                 525

Val Cys Ala Val Gly Ser Arg Asn Gly Thr Glu Thr Lys Leu Leu
            530                 535                 540

Val Leu Asp Phe Asp Val Asp Met Lys
545                 550

<210> SEQ ID NO 6
<211> LENGTH: 545
<212> TYPE: PRT
<213> ORGANISM: Homo sapiens

<400> SEQUENCE: 6

Met Ile Phe Tyr Lys Met Lys Arg Lys Leu Asp His Gly Ser Glu Val
  1               5                  10                  15

Arg Ser Phe Ser Leu Gly Lys Lys Pro Cys Lys Val Ser Glu Tyr Thr
                 20                  25                  30

Ser Thr Thr Gly Leu Val Pro Cys Ser Ala Thr Pro Thr Thr Phe Gly
             35                  40                  45

Asp Leu Arg Ala Ala Asn Gly Gln Gly Gln Gln Arg Arg Arg Ile Thr
         50                  55                  60

Ser Val Gln Pro Pro Thr Gly Leu Gln Glu Trp Leu Lys Met Phe Gln
 65                  70                  75                  80

Ser Trp Ser Gly Pro Glu Lys Leu Leu Ala Leu Asp Glu Leu Ile Asp
                 85                  90                  95

Ser Cys Glu Pro Thr Gln Val Lys His Met Met Gln Val Ile Glu Pro
                100                 105                 110

Gln Phe Gln Arg Asp Phe Ile Ser Leu Leu Pro Lys Glu Leu Ala Leu
            115                 120                 125

Tyr Val Leu Ser Phe Leu Glu Pro Lys Asp Leu Leu Gln Ala Ala Gln
        130                 135                 140

Thr Cys Arg Tyr Trp Arg Ile Leu Ala Glu Asp Asn Leu Leu Trp Arg
145                 150                 155                 160

Glu Lys Cys Lys Glu Glu Gly Ile Asp Glu Pro Leu His Ile Lys Arg
                165                 170                 175

Arg Lys Val Ile Lys Pro Gly Phe Ile His Ser Pro Trp Lys Ser Ala
            180                 185                 190

Tyr Ile Arg Gln His Arg Ile Asp Thr Asn Trp Arg Arg Gly Glu Leu
        195                 200                 205

Lys Ser Pro Lys Val Leu Lys Gly His Asp Asp His Val Ile Thr Cys
210                 215                 220

Leu Gln Phe Cys Gly Asn Arg Ile Val Ser Gly Ser Asp Asp Asn Thr
225                 230                 235                 240

Leu Lys Val Trp Ser Ala Val Thr Gly Lys Cys Leu Arg Thr Leu Val
                245                 250                 255

Gly His Thr Gly Gly Val Trp Ser Ser Gln Met Arg Asp Asn Ile Ile
            260                 265                 270

Ile Ser Gly Ser Thr Asp Arg Thr Leu Lys Val Trp Asn Ala Glu Thr
        275                 280                 285

Gly Glu Cys Ile His Thr Leu Tyr Gly His Thr Ser Thr Val Arg Cys
    290                 295                 300
```

```
Met His Leu His Glu Lys Arg Val Ser Gly Ser Arg Asp Ala Thr
305                 310                 315                 320

Leu Arg Val Trp Asp Ile Glu Thr Gly Gln Cys Leu His Val Leu Met
            325                 330                 335

Gly His Val Ala Ala Val Arg Cys Val Gln Tyr Asp Gly Arg Arg Val
            340                 345                 350

Val Ser Gly Ala Tyr Asp Phe Met Val Lys Val Trp Asp Pro Glu Thr
        355                 360                 365

Glu Thr Cys Leu His Thr Leu Gln Gly His Thr Asn Arg Val Tyr Ser
370                 375                 380

Leu Gln Phe Asp Gly Ile His Val Val Ser Gly Ser Leu Asp Thr Ser
385                 390                 395                 400

Ile Arg Val Trp Asp Val Glu Thr Gly Asn Cys Ile His Thr Leu Thr
            405                 410                 415

Gly His Gln Ser Leu Thr Ser Gly Met Glu Leu Lys Asp Asn Ile Leu
        420                 425                 430

Val Ser Gly Asn Ala Asp Ser Thr Val Lys Ile Trp Asp Ile Lys Thr
        435                 440                 445

Gly Gln Cys Leu Gln Thr Leu Gln Gly Pro Asn Lys His Gln Ser Ala
    450                 455                 460

Val Thr Cys Leu Gln Phe Asn Lys Asn Phe Val Ile Thr Ser Ser Asp
465                 470                 475                 480

Asp Gly Thr Val Lys Leu Trp Asp Leu Lys Thr Gly Glu Phe Ile Arg
            485                 490                 495

Asn Leu Val Thr Leu Glu Ser Gly Gly Ser Gly Gly Val Val Trp Arg
                500                 505                 510

Ile Arg Ala Ser Asn Thr Lys Leu Val Cys Ala Val Gly Ser Arg Asn
            515                 520                 525

Gly Thr Glu Glu Thr Lys Leu Leu Val Leu Asp Phe Asp Val Asp Met
        530                 535                 540

Lys
545

<210> SEQ ID NO 7
<211> LENGTH: 540
<212> TYPE: PRT
<213> ORGANISM: Homo sapiens

<400> SEQUENCE: 7

Met Lys Arg Lys Leu Asp His Gly Ser Glu Val Arg Ser Phe Ser Leu
1               5                   10                  15

Gly Lys Lys Pro Cys Lys Val Ser Glu Tyr Thr Ser Thr Thr Gly Leu
            20                  25                  30

Val Pro Cys Ser Ala Thr Pro Thr Thr Phe Gly Asp Leu Arg Ala Ala
        35                  40                  45

Asn Gly Gln Gly Gln Gln Arg Arg Ile Thr Ser Val Gln Pro Pro
    50                  55                  60

Thr Gly Leu Gln Glu Trp Leu Lys Met Phe Gln Ser Trp Ser Gly Pro
65                  70                  75                  80

Glu Lys Leu Leu Ala Leu Asp Glu Leu Ile Asp Ser Cys Glu Pro Thr
                85                  90                  95

Gln Val Lys His Met Met Gln Val Ile Glu Pro Gln Phe Gln Arg Asp
            100                 105                 110

Phe Ile Ser Leu Leu Pro Lys Glu Leu Ala Leu Tyr Val Leu Ser Phe
        115                 120                 125
```

```
Leu Glu Pro Lys Asp Leu Leu Gln Ala Ala Gln Thr Cys Arg Tyr Trp
    130                 135                 140

Arg Ile Leu Ala Glu Asp Asn Leu Leu Trp Arg Glu Lys Cys Lys Glu
145                 150                 155                 160

Glu Gly Ile Asp Glu Pro Leu His Ile Lys Arg Lys Val Ile Lys
                165                 170                 175

Pro Gly Phe Ile His Ser Pro Trp Lys Ser Ala Tyr Ile Arg Gln His
                180                 185                 190

Arg Ile Asp Thr Asn Trp Arg Arg Gly Glu Leu Lys Ser Pro Lys Val
        195                 200                 205

Leu Lys Gly His Asp Asp His Val Ile Thr Cys Leu Gln Phe Cys Gly
        210                 215                 220

Asn Arg Ile Val Ser Gly Ser Asp Asp Asn Thr Leu Lys Val Trp Ser
225                 230                 235                 240

Ala Val Thr Gly Lys Cys Leu Arg Thr Leu Val Gly His Thr Gly Gly
                245                 250                 255

Val Trp Ser Ser Gln Met Arg Asp Asn Ile Ile Ile Ser Gly Ser Thr
                260                 265                 270

Asp Arg Thr Leu Lys Val Trp Asn Ala Glu Thr Gly Glu Cys Ile His
        275                 280                 285

Thr Leu Tyr Gly His Thr Ser Thr Val Arg Cys Met His Leu His Glu
        290                 295                 300

Lys Arg Val Val Ser Gly Ser Arg Asp Ala Thr Leu Arg Val Trp Asp
305                 310                 315                 320

Ile Glu Thr Gly Gln Cys Leu His Val Leu Met Gly His Val Ala Ala
                325                 330                 335

Val Arg Cys Val Gln Tyr Asp Gly Arg Arg Val Val Ser Gly Ala Tyr
                340                 345                 350

Asp Phe Met Val Lys Val Trp Asp Pro Glu Thr Glu Thr Cys Leu His
            355                 360                 365

Thr Leu Gln Gly His Thr Asn Arg Val Tyr Ser Leu Gln Phe Asp Gly
        370                 375                 380

Ile His Val Val Ser Gly Ser Leu Asp Thr Ser Ile Arg Val Trp Asp
385                 390                 395                 400

Val Glu Thr Gly Asn Cys Ile His Thr Leu Thr Gly His Gln Ser Leu
                405                 410                 415

Thr Ser Gly Met Glu Leu Lys Asn Ile Leu Val Ser Gly Asn Ala
                420                 425                 430

Asp Ser Thr Val Lys Ile Trp Asp Ile Lys Thr Gly Gln Cys Leu Gln
            435                 440                 445

Thr Leu Gln Gly Pro Asn Lys His Gln Ser Ala Val Thr Cys Leu Gln
        450                 455                 460

Phe Asn Lys Asn Phe Val Ile Thr Ser Ser Asp Asp Gly Thr Val Lys
465                 470                 475                 480

Leu Trp Asp Leu Lys Thr Gly Glu Phe Ile Arg Asn Leu Val Thr Leu
                485                 490                 495

Glu Ser Gly Gly Ser Gly Gly Val Val Trp Arg Ile Arg Ala Ser Asn
                500                 505                 510

Thr Lys Leu Val Cys Ala Val Gly Ser Arg Asn Gly Thr Glu Glu Thr
        515                 520                 525

Lys Leu Leu Val Leu Asp Phe Asp Val Asp Met Lys
530                 535                 540
```

<210> SEQ ID NO 8
<211> LENGTH: 589
<212> TYPE: PRT
<213> ORGANISM: Homo sapiens

<400> SEQUENCE: 8

Met Ser Lys Pro Gly Lys Pro Thr Leu Asn His Gly Leu Val Pro Val
 1               5                  10                  15

Asp Leu Lys Ser Ala Lys Glu Pro Leu Pro His Gln Thr Val Met Lys
                20                  25                  30

Ile Phe Ser Ile Ser Ile Ile Ala Gln Gly Leu Pro Phe Cys Arg Arg
            35                  40                  45

Arg Met Lys Arg Lys Leu Asp His Gly Ser Glu Val Arg Ser Phe Ser
 50                  55                  60

Leu Gly Lys Lys Pro Cys Lys Val Ser Glu Tyr Thr Ser Thr Thr Gly
 65                  70                  75                  80

Leu Val Pro Cys Ser Ala Thr Pro Thr Thr Phe Gly Asp Leu Arg Ala
                85                  90                  95

Ala Asn Gly Gln Gly Gln Gln Arg Arg Arg Ile Thr Ser Val Gln Pro
            100                 105                 110

Pro Thr Gly Leu Gln Glu Trp Leu Lys Met Phe Gln Ser Trp Ser Gly
        115                 120                 125

Pro Glu Lys Leu Leu Ala Leu Asp Glu Leu Ile Asp Ser Cys Glu Pro
130                 135                 140

Thr Gln Val Lys His Met Met Gln Val Ile Glu Pro Gln Phe Gln Arg
145                 150                 155                 160

Asp Phe Ile Ser Leu Leu Pro Lys Glu Leu Ala Leu Tyr Val Leu Ser
                165                 170                 175

Phe Leu Glu Pro Lys Asp Leu Leu Gln Ala Ala Gln Thr Cys Arg Tyr
            180                 185                 190

Trp Arg Ile Leu Ala Glu Asp Asn Leu Leu Trp Arg Glu Lys Cys Lys
        195                 200                 205

Glu Glu Gly Ile Asp Glu Pro Leu His Ile Lys Arg Arg Lys Val Ile
210                 215                 220

Lys Pro Gly Phe Ile His Ser Pro Trp Lys Ser Ala Tyr Ile Arg Gln
225                 230                 235                 240

His Arg Ile Asp Thr Asn Trp Arg Arg Gly Glu Leu Lys Ser Pro Lys
                245                 250                 255

Val Leu Lys Gly His Asp Asp His Val Ile Thr Cys Leu Gln Phe Cys
            260                 265                 270

Gly Asn Arg Ile Val Ser Gly Ser Asp Asp Asn Thr Leu Lys Val Trp
        275                 280                 285

Ser Ala Val Thr Gly Lys Cys Leu Arg Thr Leu Val Gly His Thr Gly
290                 295                 300

Gly Val Trp Ser Ser Gln Met Arg Asp Asn Ile Ile Ile Ser Gly Ser
305                 310                 315                 320

Thr Asp Arg Thr Leu Lys Val Trp Asn Ala Glu Thr Gly Glu Cys Ile
                325                 330                 335

His Thr Leu Tyr Gly His Thr Ser Thr Val Arg Cys Met His Leu His
            340                 345                 350

Glu Lys Arg Val Val Ser Gly Ser Arg Asp Ala Thr Leu Arg Val Trp
        355                 360                 365

Asp Ile Glu Thr Gly Gln Cys Leu His Val Leu Met Gly His Val Ala
370                 375                 380

```
Ala Val Arg Cys Val Gln Tyr Asp Gly Arg Arg Val Ser Gly Ala
385                 390                 395                 400

Tyr Asp Phe Met Val Lys Val Trp Asp Pro Glu Thr Glu Thr Cys Leu
            405                 410                 415

His Thr Leu Gln Gly His Thr Asn Arg Val Tyr Ser Leu Gln Phe Asp
            420                 425                 430

Gly Ile His Val Ser Gly Ser Leu Asp Thr Ser Ile Arg Val Trp
            435                 440                 445

Asp Val Glu Thr Gly Asn Cys Ile His Thr Leu Thr Gly His Gln Ser
450                 455                 460

Leu Thr Ser Gly Met Glu Leu Lys Asp Asn Ile Leu Val Ser Gly Asn
465                 470                 475                 480

Ala Asp Ser Thr Val Lys Ile Trp Asp Ile Lys Thr Gly Gln Cys Leu
                485                 490                 495

Gln Thr Leu Gln Gly Pro Asn Lys His Gln Ser Ala Val Thr Cys Leu
            500                 505                 510

Gln Phe Asn Lys Asn Phe Val Ile Thr Ser Ser Asp Asp Gly Thr Val
            515                 520                 525

Lys Leu Trp Asp Leu Lys Thr Gly Glu Phe Ile Arg Asn Leu Val Thr
530                 535                 540

Leu Glu Ser Gly Gly Ser Gly Gly Val Val Trp Arg Ile Arg Ala Ser
545                 550                 555                 560

Asn Thr Lys Leu Val Cys Ala Val Gly Ser Arg Asn Gly Thr Glu Glu
                565                 570                 575

Thr Lys Leu Leu Val Leu Asp Phe Asp Val Asp Met Lys
            580                 585

<210> SEQ ID NO 9
<211> LENGTH: 559
<212> TYPE: PRT
<213> ORGANISM: Homo sapiens

<400> SEQUENCE: 9

Met Lys Ile Phe Ser Ile Ser Ile Ile Ala Gln Gly Leu Pro Phe Cys
1               5                   10                  15

Arg Arg Arg Met Lys Arg Lys Leu Asp His Gly Ser Glu Val Arg Ser
            20                  25                  30

Phe Ser Leu Gly Lys Lys Pro Cys Lys Val Ser Glu Tyr Thr Ser Thr
        35                  40                  45

Thr Gly Leu Val Pro Cys Ser Ala Thr Pro Thr Thr Phe Gly Asp Leu
    50                  55                  60

Arg Ala Ala Asn Gly Gln Gly Gln Gln Arg Arg Ile Thr Ser Val
65                  70                  75                  80

Gln Pro Pro Thr Gly Leu Gln Glu Trp Leu Lys Met Phe Gln Ser Trp
                85                  90                  95

Ser Gly Pro Glu Lys Leu Leu Ala Leu Asp Glu Leu Ile Asp Ser Cys
            100                 105                 110

Glu Pro Thr Gln Val Lys His Met Met Gln Val Ile Glu Pro Gln Phe
        115                 120                 125

Gln Arg Asp Phe Ile Ser Leu Leu Pro Lys Glu Leu Ala Leu Tyr Val
    130                 135                 140

Leu Ser Phe Leu Glu Pro Lys Asp Leu Leu Gln Ala Ala Gln Thr Cys
145                 150                 155                 160

Arg Tyr Trp Arg Ile Leu Ala Glu Asp Asn Leu Leu Trp Arg Glu Lys
```

165                 170                 175
Cys Lys Glu Glu Gly Ile Asp Glu Pro Leu His Ile Lys Arg Arg Lys
                180                 185                 190
Val Ile Lys Pro Gly Phe Ile His Ser Pro Trp Lys Ser Ala Tyr Ile
            195                 200                 205
Arg Gln His Arg Ile Asp Thr Asn Trp Arg Arg Gly Glu Leu Lys Ser
        210                 215                 220
Pro Lys Val Leu Lys Gly His Asp His Val Ile Thr Cys Leu Gln
225                 230                 235                 240
Phe Cys Gly Asn Arg Ile Val Ser Gly Ser Asp Asn Thr Leu Lys
                245                 250                 255
Val Trp Ser Ala Val Thr Gly Lys Cys Leu Arg Thr Leu Val Gly His
            260                 265                 270
Thr Gly Gly Val Trp Ser Ser Gln Met Arg Asp Asn Ile Ile Ile Ser
        275                 280                 285
Gly Ser Thr Asp Arg Thr Leu Lys Val Trp Asn Ala Glu Thr Gly Glu
    290                 295                 300
Cys Ile His Thr Leu Tyr Gly His Thr Ser Thr Val Arg Cys Met His
305                 310                 315                 320
Leu His Glu Lys Arg Val Val Ser Gly Ser Arg Asp Ala Thr Leu Arg
                325                 330                 335
Val Trp Asp Ile Glu Thr Gly Gln Cys Leu His Val Leu Met Gly His
            340                 345                 350
Val Ala Ala Val Arg Cys Val Gln Tyr Asp Gly Arg Arg Val Val Ser
        355                 360                 365
Gly Ala Tyr Asp Phe Met Val Lys Val Trp Asp Pro Glu Thr Glu Thr
    370                 375                 380
Cys Leu His Thr Leu Gln Gly His Thr Asn Arg Val Tyr Ser Leu Gln
385                 390                 395                 400
Phe Asp Gly Ile His Val Val Ser Gly Ser Leu Asp Thr Ser Ile Arg
                405                 410                 415
Val Trp Asp Val Glu Thr Gly Asn Cys Ile His Thr Leu Thr Gly His
            420                 425                 430
Gln Ser Leu Thr Ser Gly Met Glu Leu Lys Asp Asn Ile Leu Val Ser
        435                 440                 445
Gly Asn Ala Asp Ser Thr Val Lys Ile Trp Asp Ile Lys Thr Gly Gln
    450                 455                 460
Cys Leu Gln Thr Leu Gln Gly Pro Asn Lys His Gln Ser Ala Val Thr
465                 470                 475                 480
Cys Leu Gln Phe Asn Lys Asn Phe Val Ile Thr Ser Ser Asp Asp Gly
                485                 490                 495
Thr Val Lys Leu Trp Asp Leu Lys Thr Gly Glu Phe Ile Arg Asn Leu
            500                 505                 510
Val Thr Leu Glu Ser Gly Gly Ser Gly Gly Val Val Trp Arg Ile Arg
        515                 520                 525
Ala Ser Asn Thr Lys Leu Val Cys Ala Val Gly Ser Arg Asn Gly Thr
    530                 535                 540
Glu Glu Thr Lys Leu Leu Val Leu Asp Phe Asp Val Asp Met Lys
545                 550                 555

<210> SEQ ID NO 10
<211> LENGTH: 540
<212> TYPE: PRT
<213> ORGANISM: Homo sapiens

<400> SEQUENCE: 10

Met Lys Arg Lys Leu Asp His Gly Ser Glu Val Arg Ser Phe Ser Leu
1               5                   10                  15

Gly Lys Lys Pro Cys Lys Val Ser Glu Tyr Thr Ser Thr Thr Gly Leu
            20                  25                  30

Val Pro Cys Ser Ala Thr Pro Thr Thr Phe Gly Asp Leu Arg Ala Ala
        35                  40                  45

Asn Gly Gln Gly Gln Gln Arg Arg Ile Thr Ser Val Gln Pro Pro
    50                  55                  60

Thr Gly Leu Gln Glu Trp Leu Lys Met Phe Gln Ser Trp Ser Gly Pro
65                  70                  75                  80

Glu Lys Leu Leu Ala Leu Asp Glu Leu Ile Asp Ser Cys Glu Pro Thr
                85                  90                  95

Gln Val Lys His Met Met Gln Val Ile Glu Pro Gln Phe Gln Arg Asp
            100                 105                 110

Phe Ile Ser Leu Leu Pro Lys Glu Leu Ala Leu Tyr Val Leu Ser Phe
        115                 120                 125

Leu Glu Pro Lys Asp Leu Leu Gln Ala Ala Gln Thr Cys Arg Tyr Trp
130                 135                 140

Arg Ile Leu Ala Glu Asp Asn Leu Leu Trp Arg Glu Lys Cys Lys Glu
145                 150                 155                 160

Glu Gly Ile Asp Glu Pro Leu His Ile Lys Arg Lys Val Ile Lys
                165                 170                 175

Pro Gly Phe Ile His Ser Pro Trp Lys Ser Ala Tyr Ile Arg Gln His
            180                 185                 190

Arg Ile Asp Thr Asn Trp Arg Arg Gly Glu Leu Lys Ser Pro Lys Val
        195                 200                 205

Leu Lys Gly His Asp Asp His Val Ile Thr Cys Leu Gln Phe Cys Gly
210                 215                 220

Asn Arg Ile Val Ser Gly Ser Asp Asp Asn Thr Leu Lys Val Trp Ser
225                 230                 235                 240

Ala Val Thr Gly Lys Cys Leu Arg Thr Leu Val Gly His Thr Gly Gly
                245                 250                 255

Val Trp Ser Ser Gln Met Arg Asp Asn Ile Ile Ser Gly Ser Thr
            260                 265                 270

Asp Arg Thr Leu Lys Val Trp Asn Ala Glu Thr Gly Glu Cys Ile His
        275                 280                 285

Thr Leu Tyr Gly His Thr Ser Thr Val Arg Cys Met His Leu His Glu
290                 295                 300

Lys Arg Val Val Ser Gly Ser Arg Asp Ala Thr Leu Arg Val Trp Asp
305                 310                 315                 320

Ile Glu Thr Gly Gln Cys Leu His Val Leu Met Gly His Val Ala Ala
                325                 330                 335

Val Arg Cys Val Gln Tyr Asp Gly Arg Arg Val Val Ser Gly Ala Tyr
            340                 345                 350

Asp Phe Met Val Lys Val Trp Asp Pro Glu Thr Glu Thr Cys Leu His
        355                 360                 365

Thr Leu Gln Gly His Thr Asn Arg Val Tyr Ser Leu Gln Phe Asp Gly
370                 375                 380

Ile His Val Val Ser Gly Ser Leu Asp Thr Ser Ile Arg Val Trp Asp
385                 390                 395                 400

Val Glu Thr Gly Asn Cys Ile His Thr Leu Thr Gly His Gln Ser Leu

```
                    405                 410                 415
Thr Ser Gly Met Glu Leu Lys Asp Asn Ile Leu Val Ser Gly Asn Ala
            420                 425                 430

Asp Ser Thr Val Lys Ile Trp Asp Ile Lys Thr Gly Gln Cys Leu Gln
        435                 440                 445

Thr Leu Gln Gly Pro Asn Lys His Gln Ser Ala Val Thr Cys Leu Gln
    450                 455                 460

Phe Asn Lys Asn Phe Val Ile Thr Ser Ser Asp Asp Gly Thr Val Lys
465                 470                 475                 480

Leu Trp Asp Leu Lys Thr Gly Glu Phe Ile Arg Asn Leu Val Thr Leu
                485                 490                 495

Glu Ser Gly Gly Ser Gly Gly Val Val Trp Arg Ile Arg Ala Ser Asn
            500                 505                 510

Thr Lys Leu Val Cys Ala Val Gly Ser Arg Asn Gly Thr Glu Glu Thr
        515                 520                 525

Lys Leu Leu Val Leu Asp Phe Asp Val Asp Met Lys
    530                 535                 540
```

<210> SEQ ID NO 11
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 11
cgggatccac catggatgat ggatcgatga cacc                    34

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 12
ggaattcctt aagggtatac agcatcaaag tcg                     33

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 13
tcacttcatg tccacatcaa agtcc                              25

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 14
ggtaattaca agttcttgtt gaactg                             26

```
<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 15
ccctgcaacg tgtgtagaca gg                                            22

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 16
ccagtctctg cattccacac tttg                                          24

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 17
ctcagacagg tcaggacatt tgg                                           23

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 18
ggaattccat gaaaagattg gaccatggtt ctg                                33

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 19
ggaattcctc acttcatgtc acatcaaagt ccag                               34

<210> SEQ ID NO 20
<211> LENGTH: 1881
<212> TYPE: DNA
<213> ORGANISM: Artificial Sequence
<220> FEATURE:
<223> OTHER INFORMATION: Description of Artificial Sequence:  6 myc
      tagged homo sapiens

<400> SEQUENCE: 20
atggagcaaa agctcatttc tgaagaggac ttgaatgaaa tggagcaaaa gctcatttct    60
gaagaggact tgaatgaaat ggagcaaaag ctcatttctg aagaggactt gaatgaaatg   120
```

-continued

```
gagcaaaagc tcatttctga agaggacttg aatgaaatgg agcaaaagct catttctgaa      180
gaggacttga atgaaatgga gagcttgggc gacctcacca tggagcaaaa gctcatttct      240
gaagaggact tgaattccat gaaaagaaag ttggaccatg gttctgaggt ccgctctttt      300
tctttgggaa agaaaccatg caaagtctca gaatatacaa gtaccactgg gcttgtacca      360
tgttcagcaa caccaacaac ttttggggac ctcagagcag ccaatggcca agggcaacaa      420
cgacgccgaa ttacatctgt ccagccacct acaggcctcc aggaatggct aaaaatgttt      480
cagagctgga gtggaccaga gaattgcttg ctttagatg aactcattga tagttgtgaa       540
ccaacacaag taaacatat gatgcaagtg atagaacccc agtttcaacg agacttcatt       600
tcattgctcc ctaaagagtt ggcactctat gtgctttcat tcctggaacc caaagacctg      660
ctacaagcag ctcagacatg tcgctactgg agaattttgg ctgaagacaa ccttctctgg      720
agagagaaat gcaaagaaga ggggattgat gaaccattgc acatcaagag aagaaaagta      780
ataaaaccag gtttcataca cagtccatgg aaaagtgcat acatcagaca gcacagaatt      840
gatactaact ggaggcgagg agaactcaaa tctcctaagg tgctgaaagg acatgatgat      900
catgtgatca catgcttaca gttttgtggt aaccgaatag ttagtggttc tgatgacaac      960
actttaaaag tttggtcagc agtcacaggc aaatgtctga gaacattagt gggacataca     1020
ggtggagtat ggtcatcaca aatgagggac aacatcatca ttagtggatc tacagatcgg     1080
acactcaaag tgtggaatgc agagactgga gaatgtatac acaccttata tgggcatact     1140
tccactgtgc gttgtatgca tcttcatgaa aaaagagttg ttagcggttc tcgagatgcc     1200
actcttaggg tttgggatat tgagacaggc cagtgtttac atgttttgat gggtcatgtt     1260
gcagcagtcc gctgtgttca atatgatggc aggagggttg ttagtggagc atatgatttt     1320
atggtaaagg tgtgggatcc agagactgaa acctgtctac acacgttgca ggggcatact     1380
aatagagtct attcattaca gtttgatggt atccatgtgg tgagtggatc tcttgataca     1440
tccatccgtg tttgggatgt ggagacaggg aattgcattc acacgttaac agggcaccag     1500
tcgttaacaa gtggaatgga actcaaagac aatattcttg tctctgggaa tgcagattct     1560
acagttaaaa tctgggatat caaaacagga cagtgtttac aaacattgca aggtcccaac     1620
aagcatcaga gtgctgtgac ctgtttacag ttcaacaaga actttgtaat taccagctca     1680
gatgatggaa ctgtaaaact atgggacttg aaaacgggtg aatttattcg aaacctagtc     1740
acattggaga gtgggggggag tggggagtt gtgtggcgga tcagagcctc aaacacaaag     1800
ctggtgtgtg cagttgggag tcggaatggg actgaagaaa ccaagctgct ggtgctggac     1860
tttgatgtgg acatgaagtg a                                                1881
```

<210> SEQ ID NO 21
<211> LENGTH: 626
<212> TYPE: PRT
<213> ORGANISM: Artificial Sequence
<220> FEATURE:
<223> OTHER INFORMATION: Description of Artificial Sequence: 6 myc
      tagged homo sapien

<400> SEQUENCE: 21

```
Met Glu Gln Lys Leu Ile Ser Glu Glu Asp Leu Asn Glu Met Glu Gln
 1               5                  10                  15

Lys Leu Ile Ser Glu Glu Asp Leu Asn Glu Met Glu Gln Lys Leu Ile
             20                  25                  30

Ser Glu Glu Asp Leu Asn Glu Met Glu Gln Lys Leu Ile Ser Glu Glu
         35                  40                  45
```

-continued

```
Asp Leu Asn Glu Met Glu Gln Lys Leu Ile Ser Glu Glu Asp Leu Asn
 50                  55                  60

Glu Met Glu Ser Leu Gly Asp Leu Thr Met Glu Gln Lys Leu Ile Ser
 65                  70                  75                  80

Glu Glu Asp Leu Asn Ser Met Lys Arg Lys Leu Asp His Gly Ser Glu
                 85                  90                  95

Val Arg Ser Phe Ser Leu Gly Lys Lys Pro Cys Lys Val Ser Glu Tyr
                100                 105                 110

Thr Ser Thr Thr Gly Leu Val Pro Cys Ser Ala Thr Pro Thr Thr Phe
            115                 120                 125

Gly Asp Leu Arg Ala Ala Asn Gly Gln Gly Gln Gln Arg Arg Arg Ile
130                 135                 140

Thr Ser Val Gln Pro Pro Thr Gly Leu Gln Glu Trp Leu Lys Met Phe
145                 150                 155                 160

Gln Ser Trp Ser Gly Pro Glu Lys Leu Leu Ala Leu Asp Glu Leu Ile
                165                 170                 175

Asp Ser Cys Glu Pro Thr Gln Val Lys His Met Met Gln Val Ile Glu
            180                 185                 190

Pro Gln Phe Gln Arg Asp Phe Ile Ser Leu Leu Pro Lys Glu Leu Ala
            195                 200                 205

Leu Tyr Val Leu Ser Phe Leu Glu Pro Lys Asp Leu Leu Gln Ala Ala
210                 215                 220

Gln Thr Cys Arg Tyr Trp Arg Ile Leu Ala Glu Asp Asn Leu Leu Trp
225                 230                 235                 240

Arg Glu Lys Cys Lys Glu Gly Ile Asp Glu Pro Leu His Ile Lys
                245                 250                 255

Arg Arg Lys Val Ile Lys Pro Gly Phe Ile His Ser Pro Trp Lys Ser
            260                 265                 270

Ala Tyr Ile Arg Gln His Arg Ile Asp Thr Asn Trp Arg Arg Gly Glu
            275                 280                 285

Leu Lys Ser Pro Lys Val Leu Lys Gly His Asp Asp His Val Ile Thr
            290                 295                 300

Cys Leu Gln Phe Cys Gly Asn Arg Ile Val Ser Gly Ser Asp Asp Asn
305                 310                 315                 320

Thr Leu Lys Val Trp Ser Ala Val Thr Gly Lys Cys Leu Arg Thr Leu
                325                 330                 335

Val Gly His Thr Gly Gly Val Trp Ser Ser Gln Met Arg Asp Asn Ile
            340                 345                 350

Ile Ile Ser Gly Ser Thr Asp Arg Thr Leu Lys Val Trp Asn Ala Glu
            355                 360                 365

Thr Gly Glu Cys Ile His Thr Leu Tyr Gly His Thr Ser Thr Val Arg
            370                 375                 380

Cys Met His Leu His Glu Lys Arg Val Val Ser Gly Ser Arg Asp Ala
385                 390                 395                 400

Thr Leu Arg Val Trp Asp Ile Glu Thr Gly Gln Cys Leu His Val Leu
                405                 410                 415

Met Gly His Val Ala Ala Val Arg Cys Val Gln Tyr Asp Gly Arg Arg
            420                 425                 430

Val Val Ser Gly Ala Tyr Asp Phe Met Val Lys Val Trp Asp Pro Glu
            435                 440                 445

Thr Glu Thr Cys Leu His Thr Leu Gln Gly His Thr Asn Arg Val Tyr
450                 455                 460
```

```
Ser Leu Gln Phe Asp Gly Ile His Val Val Ser Gly Ser Leu Asp Thr
465                 470                 475                 480

Ser Ile Arg Val Trp Asp Val Glu Thr Gly Asn Cys Ile His Thr Leu
                485                 490                 495

Thr Gly His Gln Ser Leu Thr Ser Gly Met Glu Leu Lys Asp Asn Ile
            500                 505                 510

Leu Val Ser Gly Asn Ala Asp Ser Thr Val Lys Ile Trp Asp Ile Lys
        515                 520                 525

Thr Gly Gln Cys Leu Gln Thr Leu Gln Gly Pro Asn Lys His Gln Ser
    530                 535                 540

Ala Val Thr Cys Leu Gln Phe Asn Lys Asn Phe Val Ile Thr Ser Ser
545                 550                 555                 560

Asp Asp Gly Thr Val Lys Leu Trp Asp Leu Lys Thr Gly Glu Phe Ile
                565                 570                 575

Arg Asn Leu Val Thr Leu Glu Ser Gly Gly Ser Gly Val Val Trp
            580                 585                 590

Arg Ile Arg Ala Ser Asn Thr Lys Leu Val Cys Ala Val Gly Ser Arg
        595                 600                 605

Asn Gly Thr Glu Glu Thr Lys Leu Leu Val Leu Asp Phe Asp Val Asp
    610                 615                 620

Met Lys
625

<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 22
gggtacccct cattattccc tcgagttctt c                              31

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 23
ggaattcctt catgtccaca tcaaagtcc                                 29

<210> SEQ ID NO 24
<211> LENGTH: 2010
<212> TYPE: DNA
<213> ORGANISM: Artificial Sequence
<220> FEATURE:
<223> OTHER INFORMATION: Description of Artificial Sequence: V5HIS
      tagged homo sapien

<400> SEQUENCE: 24
atgtgtgtcc cgagaagcgg tttgatactg agctgcattt gcctttactg tggagttttg    60
ttgccggttc tgctccctaa tcttcctttt ctgacgtgcc tgagcatgtc cacattagaa   120
tctgtgacat acctacctga aaaggttta tattgtcaga gactgccaag cagccggaca   180
cacgggggca cagaatcact gaaggggaaa aatacagaaa atatgggttt ctacggcaca   240
ttaaaaatga ttttttacaa aatgaaagaa agttggacc atggttctga ggtccgctct   300
```

-continued

```
ttttctttgg gaaagaaacc atgcaaagtc tcagaatata caagtaccac tgggcttgta      360
ccatgttcag caacaccaac aacttttggg gacctcagag cagccaatgg ccaagggcaa      420
caacgacgcc gaattacatc tgtccagcca cctacaggcc tccaggaatg gctaaaaatg      480
tttcagagct ggagtggacc agagaaattg cttgctttag atgaactcat tgatagttgt      540
gaaccaacac aagtaaaaca tatgatgcaa gtgatagaac cccagtttca acgagacttc      600
atttcattgc tccctaaaga gttggcactc tatgtgcttt cattcctgga acccaaagac      660
ctgctacaag cagctcagac atgtcgctac tggagaattt tggctgaaga caaccttctc      720
tggagagaga aatgcaaaga gaggggatt gatgaaccat tgcacatcaa gagaagaaaa      780
gtaataaaac caggtttcat acacagtcca tggaaaagtg catacatcag acagcacaga      840
attgatacta actggaggcg aggagaactc aaatctccta aggtgctgaa aggacatgat      900
gatcatgtga tcacatgctt acagttttgt ggtaaccgaa tagttagtgg ttctgatgac      960
aacactttaa agtttggtc agcagtcaca ggcaaatgtc tgagaacatt agtgggacat     1020
acaggtggag tatggtcatc acaaatgaga acaacatca tcattagtgg atctacagat     1080
cggacactca aagtgtggaa tgcagagact ggagaatgta tacacacctt atatgggcat     1140
acttccactg tgcgttgtat gcatcttcat gaaaaagag ttgttagcgg ttctcgagat     1200
gccactctta gggtttggga tattgagaca ggccagtgtt tacatgtttt gatgggtcat     1260
gttgcagcag tccgctgtgt tcaatatgat ggcaggaggg ttgttagtgg agcatatgat     1320
tttatggtaa aggtgtggga tccagagact gaaacctgtc tacacacgtt gcagggcat     1380 actaatagag tctattcatt acagtttgat ggtatccatg tggtgagtgg atctcttgat     1440
acatcaatcc gtgtttggga tgtggagaca gggaattgca ttcacacgtt aacagggcac     1500
cagtcgttaa caagtggaat ggaactcaaa gacaatattc ttgtctctgg gaatgcagat     1560
tctacagtta aaatctggga tatcaaaaca ggacagtgtt tacaaacatt gcaaggtccc     1620
aacaagcatc agagtgctgt gacctgttta cagttcaaca agaactttgt aattaccagc     1680
tcagatgatg gaactgtaaa actatgggac ttgaaaacgg gtgaatttat tcgaaaccta     1740
gtcacattgg agagtggggg gagtgggggga gttgtgtggc ggatcagagc ctcaaaacaca     1800 aagctggtgt gtgcagttgg gagtcggaat gggactgaag aaaccaagct gctggtgctg     1860
gactttgatg tggacatgaa ggaattctgc agatatccag cacagtggcg gccgctcgag     1920
tctagagggc ccttcgaagg taagcctatc cctaaccctc tcctcggtct cgattctacg     1980
cgtaccggtc atcatcacca tcaccattga                                      2010
```

<210> SEQ ID NO 25
<211> LENGTH: 669
<212> TYPE: PRT
<213> ORGANISM: Artificial Sequence
<220> FEATURE:
<223> OTHER INFORMATION: Description of Artificial Sequence: V5HIS
   tagged homo sapien

<400> SEQUENCE: 25

Met Cys Val Pro Arg Ser Gly Leu Ile Leu Ser Cys Ile Cys Leu Tyr
1               5                   10                  15

Cys Gly Val Leu Leu Pro Val Leu Leu Pro Asn Leu Pro Phe Leu Thr
            20                  25                  30

Cys Leu Ser Met Ser Thr Leu Glu Ser Val Thr Tyr Leu Pro Glu Lys
        35                  40                  45

```
Gly Leu Tyr Cys Gln Arg Leu Pro Ser Ser Arg Thr His Gly Gly Thr
    50                  55                  60
Glu Ser Leu Lys Gly Lys Asn Thr Glu Asn Met Gly Phe Tyr Gly Thr
65                      70                  75                  80
Leu Lys Met Ile Phe Tyr Lys Met Lys Arg Lys Leu Asp His Gly Ser
                    85                  90                  95
Glu Val Arg Ser Phe Ser Leu Gly Lys Lys Pro Cys Lys Val Ser Glu
                100                 105                 110
Tyr Thr Ser Thr Thr Gly Leu Val Pro Cys Ser Ala Thr Pro Thr Thr
            115                 120                 125
Phe Gly Asp Leu Arg Ala Ala Asn Gly Gln Gly Gln Gln Arg Arg Arg
    130                 135                 140
Ile Thr Ser Val Gln Pro Pro Thr Gly Leu Gln Glu Trp Leu Lys Met
145                 150                 155                 160
Phe Gln Ser Trp Ser Gly Pro Glu Lys Leu Leu Ala Leu Asp Glu Leu
                165                 170                 175
Ile Asp Ser Cys Glu Pro Thr Gln Val Lys His Met Met Gln Val Ile
                180                 185                 190
Glu Pro Gln Phe Gln Arg Asp Phe Ile Ser Leu Leu Pro Lys Glu Leu
            195                 200                 205
Ala Leu Tyr Val Leu Ser Phe Leu Glu Pro Lys Asp Leu Leu Gln Ala
    210                 215                 220
Ala Gln Thr Cys Arg Tyr Trp Arg Ile Leu Ala Glu Asp Asn Leu Leu
225                 230                 235                 240
Trp Arg Glu Lys Cys Lys Glu Glu Gly Ile Asp Glu Pro Leu His Ile
                245                 250                 255
Lys Arg Arg Lys Val Ile Lys Pro Gly Phe Ile His Ser Pro Trp Lys
                260                 265                 270
Ser Ala Tyr Ile Arg Gln His Arg Ile Asp Thr Asn Trp Arg Arg Gly
            275                 280                 285
Glu Leu Lys Ser Pro Lys Val Leu Lys Gly His Asp Asp His Val Ile
    290                 295                 300
Thr Cys Leu Gln Phe Cys Gly Asn Arg Ile Val Ser Gly Ser Asp Asp
305                 310                 315                 320
Asn Thr Leu Lys Val Trp Ser Ala Val Thr Gly Lys Cys Leu Arg Thr
                325                 330                 335
Leu Val Gly His Thr Gly Gly Val Trp Ser Ser Gln Met Arg Asp Asn
                340                 345                 350
Ile Ile Ile Ser Gly Ser Thr Asp Arg Thr Leu Lys Val Trp Asn Ala
            355                 360                 365
Glu Thr Gly Glu Cys Ile His Thr Leu Tyr Gly His Thr Ser Thr Val
    370                 375                 380
Arg Cys Met His Leu His Glu Lys Arg Val Val Ser Gly Ser Arg Asp
385                 390                 395                 400
Ala Thr Leu Arg Val Trp Asp Ile Glu Thr Gly Gln Cys Leu His Val
                405                 410                 415
Leu Met Gly His Val Ala Ala Val Arg Cys Val Gln Tyr Asp Gly Arg
                420                 425                 430
Arg Val Val Ser Gly Ala Tyr Asp Phe Met Val Lys Val Trp Asp Pro
            435                 440                 445
Glu Thr Glu Thr Cys Leu His Thr Leu Gln Gly His Thr Asn Arg Val
    450                 455                 460
Tyr Ser Leu Gln Phe Asp Gly Ile His Val Val Ser Gly Ser Leu Asp
```

```
                  465                 470                 475                 480
              Thr Ser Ile Arg Val Trp Asp Val Glu Thr Gly Asn Cys Ile His Thr
                                  485                 490                 495
              Leu Thr Gly His Gln Ser Leu Thr Ser Gly Met Glu Leu Lys Asp Asn
                              500                 505                 510
              Ile Leu Val Ser Gly Asn Ala Asp Ser Thr Val Lys Ile Trp Asp Ile
                          515                 520                 525
              Lys Thr Gly Gln Cys Leu Gln Thr Leu Gln Gly Pro Asn Lys His Gln
                      530                 535                 540
              Ser Ala Val Thr Cys Leu Gln Phe Asn Lys Asn Phe Val Ile Thr Ser
              545                 550                 555                 560
              Ser Asp Asp Gly Thr Val Lys Leu Trp Asp Leu Lys Thr Gly Glu Phe
                                  565                 570                 575
              Ile Arg Asn Leu Val Thr Leu Glu Ser Gly Ser Gly Gly Val Val
                              580                 585                 590
              Trp Arg Ile Arg Ala Ser Asn Thr Lys Leu Val Cys Ala Val Gly Ser
                          595                 600                 605
              Arg Asn Gly Thr Glu Glu Thr Lys Leu Leu Val Leu Asp Phe Asp Val
                      610                 615                 620
              Asp Met Lys Glu Phe Cys Arg Tyr Pro Ala Gln Trp Arg Pro Leu Glu
              625                 630                 635                 640
              Ser Arg Gly Pro Phe Glu Gly Lys Pro Ile Pro Asn Pro Leu Leu Gly
                                  645                 650                 655
              Leu Asp Ser Thr Arg Thr Gly His His His His His
                              660                 665
```

```
<210> SEQ ID NO 26
<211> LENGTH: 2001
<212> TYPE: DNA
<213> ORGANISM: Artificial Sequence
<220> FEATURE:
<223> OTHER INFORMATION: Description of Artificial Sequence:  MYCHIS
      tagged homo sapiens

<400> SEQUENCE: 26
atgtgtgtcc cgagaagcgg tttgatactg agctgcattt gcctttactg tggagttttg        60
ttgccggttc tgctccctaa tcttcctttt ctgacgtgcc tgagcatgtc cacattagaa       120
tctgtgacat acctacctga aaaaggttta tattgtcaga gactgccaag cagccggaca       180
cacgggggca cagaatcact gaagggggaaa aatacagaaa atatgggttt ctacggcaca       240
ttaaaaatga tttttttacaa aatgaaaaga agttggacc atggttctga ggtccgctct        300
ttttctttgg gaaagaaacc atgcaaagtc tcagaatata caagtaccac tgggcttgta       360
ccatgttcag caacaccaac aactttggg gacctcagag cagccaatgg ccaagggcaa        420
caacgacgcc gaattacatc tgtccagcca cctacaggcc tccaggaatg ctaaaaatg        480 tttcagagct ggagtggacc agagaaattg cttgctttag atgaactcat tgatagttgt       540
gaaccaacac aagtaaaaca tatgatgcaa gtgatagaac cccagtttca acgagacttc       600
atttcattgc tccctaaaga gttggcactc tatgtgcttt cattcctgga acccaaagac       660
ctgctacaag cagctcagac atgtcgctac tggagaattt tggctgaaga caaccttctc       720
tggagagaga atgcaaaga gaggggat gatgaaccat gcacatcaa gaagaaaaa        780 gtaataaaaac caggtttcat acacagtcca tggaaaagtg catacatcag acagcacaga       840
attgatacta actggaggcg aggagaactc aaatctccta aggtgctgaa aggacatgat       900
```

```
gatcatgtga tcacatgctt acagttttgt ggtaaccgaa tagttagtgg ttctgatgac    960
aacactttaa agtttggtc agcagtcaca ggcaaatgtc tgagaacatt agtgggacat   1020
acaggtggag tatggtcatc acaaatgaga acaacatca tcattagtgg atctacagat   1080
cggacactca aagtgtggaa tgcagagact ggagaatgta tacacacctt atatgggcat   1140
acttccactg tgcgttgtat gcatcttcat gaaaaaagag ttgttagcgg ttctcgagat   1200
gccactctta gggtttggga tattgagaca ggccagtgtt tacatgtttt gatgggtcat   1260
gttgcagcag tccgctgtgt tcaatatgat ggcaggaggg ttgttagtgg agcatatgat   1320
tttatggtaa aggtgtggga tccagagact gaaacctgtc tacacacgtt gcagggcat    1380
actaatagag tctattcatt acagtttgat ggtatccatg tggtgagtgg atctcttgat   1440
acatcaatcc gtgtttggga tgtggagaca gggaattgca ttcacacgtt aacagggcac   1500
cagtcgttaa caagtggaat ggaactcaaa gacaatattc ttgtctctgg gaatgcagat   1560
tctacagtta aaatctggga tatcaaaaca ggacagtgtt tacaaacatt gcaaggtccc   1620
aacaagcatc agagtgctgt gacctgttta cagttcaaca gaactttgt aattaccagc    1680
tcagatgatg gaactgtaaa actatgggac ttgaaaacgg gtgaatttat tcgaaaccta   1740
gtcacattgg agagtggggg gagtggggga gttgtgtggc ggatcagagc ctcaaacaca   1800
aagctggtgt gtgcagttgg gagtcggaat gggactgaag aaaccaagct gctggtgctg   1860
gactttgatg tggacatgaa ggaattctgc agatatccag cacagtggcg gccgctcgag   1920
tctagagggc ccttcgaaca aaactcatc tcagaagagg atctgaatat gcataccggt    1980
catcatcacc atcaccattg a                                             2001
```

<210> SEQ ID NO 27
<211> LENGTH: 666
<212> TYPE: PRT
<213> ORGANISM: Artificial Sequence
<220> FEATURE:
<223> OTHER INFORMATION: Description of Artificial Sequence: MYCHIS
     tagged homo sapiens

<400> SEQUENCE: 27

```
Met Cys Val Pro Arg Ser Gly Leu Ile Leu Ser Cys Ile Cys Leu Tyr
 1               5                  10                  15

Cys Gly Val Leu Leu Pro Val Leu Leu Pro Asn Leu Pro Phe Leu Thr
            20                  25                  30

Cys Leu Ser Met Ser Thr Leu Glu Ser Val Thr Tyr Leu Pro Glu Lys
        35                  40                  45

Gly Leu Tyr Cys Gln Arg Leu Pro Ser Ser Arg Thr His Gly Gly Thr
    50                  55                  60

Glu Ser Leu Lys Gly Lys Asn Thr Glu Asn Met Gly Phe Tyr Gly Thr
65                  70                  75                  80

Leu Lys Met Ile Phe Tyr Lys Met Lys Arg Lys Leu Asp His Gly Ser
                85                  90                  95

Glu Val Arg Ser Phe Ser Leu Gly Lys Lys Pro Cys Lys Val Ser Glu
            100                 105                 110

Tyr Thr Ser Thr Thr Gly Leu Val Pro Cys Ser Ala Thr Pro Thr Thr
        115                 120                 125

Phe Gly Asp Leu Arg Ala Ala Asn Gly Gln Gly Gln Gln Arg Arg Arg
    130                 135                 140

Ile Thr Ser Val Gln Pro Pro Thr Gly Leu Gln Glu Trp Leu Lys Met
145                 150                 155                 160
```

-continued

```
Phe Gln Ser Trp Ser Gly Pro Glu Lys Leu Leu Ala Leu Asp Glu Leu
            165                 170                 175
Ile Asp Ser Cys Glu Pro Thr Gln Val Lys His Met Met Gln Val Ile
        180                 185                 190
Glu Pro Gln Phe Gln Arg Asp Phe Ile Ser Leu Leu Pro Lys Glu Leu
    195                 200                 205
Ala Leu Tyr Val Leu Ser Phe Leu Glu Pro Lys Asp Leu Leu Gln Ala
210                 215                 220
Ala Gln Thr Cys Arg Tyr Trp Arg Ile Leu Ala Glu Asp Asn Leu Leu
225                 230                 235                 240
Trp Arg Glu Lys Cys Lys Glu Glu Gly Ile Asp Glu Pro Leu His Ile
                245                 250                 255
Lys Arg Arg Lys Val Ile Lys Pro Gly Phe Ile His Ser Pro Trp Lys
            260                 265                 270
Ser Ala Tyr Ile Arg Gln His Arg Ile Asp Thr Asn Trp Arg Arg Gly
        275                 280                 285
Glu Leu Lys Ser Pro Lys Val Leu Lys Gly His Asp Asp His Val Ile
    290                 295                 300
Thr Cys Leu Gln Phe Cys Gly Asn Arg Ile Val Ser Gly Ser Asp Asp
305                 310                 315                 320
Asn Thr Leu Lys Val Trp Ser Ala Val Thr Gly Lys Cys Leu Arg Thr
                325                 330                 335
Leu Val Gly His Thr Gly Gly Val Trp Ser Ser Gln Met Arg Asp Asn
            340                 345                 350
Ile Ile Ile Ser Gly Ser Thr Asp Arg Thr Leu Lys Val Trp Asn Ala
        355                 360                 365
Glu Thr Gly Glu Cys Ile His Thr Leu Tyr Gly His Thr Ser Thr Val
    370                 375                 380
Arg Cys Met His Leu His Glu Lys Arg Val Val Ser Gly Ser Arg Asp
385                 390                 395                 400
Ala Thr Leu Arg Val Trp Asp Ile Glu Thr Gly Gln Cys Leu His Val
                405                 410                 415
Leu Met Gly His Val Ala Ala Val Arg Cys Val Gln Tyr Asp Gly Arg
            420                 425                 430
Arg Val Val Ser Gly Ala Tyr Asp Phe Met Val Lys Val Trp Asp Pro
        435                 440                 445
Glu Thr Glu Thr Cys Leu His Thr Leu Gln Gly His Thr Asn Arg Val
    450                 455                 460
Tyr Ser Leu Gln Phe Asp Gly Ile His Val Val Ser Gly Ser Leu Asp
465                 470                 475                 480
Thr Ser Ile Arg Val Trp Asp Val Glu Thr Gly Asn Cys Ile His Thr
                485                 490                 495
Leu Thr Gly His Gln Ser Leu Thr Ser Gly Met Glu Leu Lys Asp Asn
            500                 505                 510
Ile Leu Val Ser Gly Asn Ala Asp Ser Thr Val Lys Ile Trp Asp Ile
        515                 520                 525
Lys Thr Gly Gln Cys Leu Gln Thr Leu Gln Gly Pro Asn Lys His Gln
    530                 535                 540
Ser Ala Val Thr Cys Leu Gln Phe Asn Lys Asn Phe Val Ile Thr Ser
545                 550                 555                 560
Ser Asp Asp Gly Thr Val Lys Leu Trp Asp Leu Lys Thr Gly Glu Phe
                565                 570                 575
Ile Arg Asn Leu Val Thr Leu Glu Ser Gly Gly Ser Gly Gly Val Val
```

```
                    580                 585                 590
Trp Arg Ile Arg Ala Ser Asn Thr Lys Leu Val Cys Ala Val Gly Ser
        595                 600                 605

Arg Asn Gly Thr Glu Glu Thr Lys Leu Leu Val Leu Asp Phe Asp Val
    610                 615                 620

Asp Met Lys Glu Phe Cys Arg Tyr Pro Ala Gln Trp Arg Pro Leu Glu
625                 630                 635                 640

Ser Arg Gly Pro Phe Glu Gln Lys Leu Ile Ser Glu Glu Asp Leu Asn
                645                 650                 655

Met His Thr Gly His His His His His His
                660                 665
1
3
```

HUMAN SEL-10 POLYPEPTIDES AND POLYNUCLEOTIDES THAT ENCODE THEM

CROSS-REFERENCE TO RELATED APPLICATIONS

This application claims the benefit of the following provisional application: U.S. Ser. No. 60/068,243, filed Dec. 19, 1997, under 35 USC 119(e)(1).

FIELD OF THE INVENTION

The present invention provides isolated nucleic acid molecules comprising a polynucleotide encoding either of two alternative splice variants of human sel-10, one of which is expressed in hippocampal cells, and one of which is expressed in mammary cells. The invention also provides isolated sel-10 polypeptides.

BACKGROUND OF THE INVENTION

Alzheimer's disease (AD) is a degenerative disorder of the central nervous system which causes progressive memory and cognitive decline during mid to late adult life. The disease is accompanied by a wide range of neuropathologic features including extracellular amyloid plaques and intra-neuronal neurofibrillary tangles. (Sherrington, R., et al.; *Nature* 375: 754–60 (1995)). Although the pathogenic pathway leading to AD is not well understood, several genetic loci are known to be involved in the development of the disease.

Genes associated with early onset Alzheimer's disease (AD) have been identified by the use of mapping studies in families with early-onset AD. These studies have shown that genetic loci on chromosomes 1 and 14 were likely to be involved in AD. Positional cloning of the chromosome 14 locus identified a novel mutant gene encoding an eight-transmembrane domain protein which subsequently was named presenilin-1 (PS-1). (Sherrington, R., et al.; *Nature* 375: 754–60 (1995)). Blast search of the human EST database revealed a single EST exhibiting homology to PS-1, designated presenilin-2 (PS-2) which was shown to be the gene associated with AD on chromosome 1. (Levy-Lahad, E. et al., *Science* 269:973–977 (1995); Rogaev, E. I., et al., *Nature* 376: 775–8 (1995); Li, J. et al., *Proc. Natl. Acad. Sci. U.S.A.* 92: 12180–12184 (1995)).

Mutations in PS-1 and PS-2 that are associated with Alzheimer's disease are primarily missense mutations. Both PS-1 and PS-2 undergo proteolytic processing, which can be altered by the point mutations found in familial Alzheimer's disease [Perez-Tur, J. et al., *Neuroreport* 7: 297–301 (1995); Mercken, M. et al., *FEBS Lett.* 389: 297–303 (1996)]. PS-1 gene expression is widely distributed across tissues, while the highest levels of PS-2 mRNA are found in pancreas and skeletal muscle. (Li, J. et al., *Proc. Natl. Acad. Sci. U.S.A.* 92: 12180–12184 (1995); Jinhe Li, personal communication). The highest levels of PS-2 protein, however, are found in brain (Jinhe Li, personal communication). Both PS-1 and PS-2 proteins have been localized to the endoplasmic reticulum, the Golgi apparatus, and the nuclear envelope. (Jinhe Li, personal communication; Kovacs, D. M. et al., *Nat. Med.* 2:224–229 (1996); Doan, A. et al., *Neuron* 17: 1023–1030 (1996)). Mutations in either the PS-1 gene or the PS-2 gene alter the processing of the amyloid protein precursor (APP) such that the ratio of A-beta$_{1-42}$ is increased relative to A-beta$_{1-40}$ (Scheuner, D. et al., *Nat. Med.* 2: 864–870 (1996)). When coexpressed in transgenic mice with human APP, a similar increase in the ratio of A-beta$_{1-42}$ as compared to A-beta$_{1-40}$ is observed (Borchelt, D. R. et al., *Neuron* 17: 1005–1013 (1996); Citron, M. et al., *Nat. Med.* 3: 67–72 (1997); Duff, K. et al., *Nature* 383: 710–713 (1996)), together with an acceleration of the deposition of A-beta in amyloid plaques (Borchelt et al., *Neuron* 19: 939 (1997).

Despite the above-described observations made with respect to the role of PS-1 and PS-2 in AD, their biological function remains unknown, placing them alongside a large number of human disease genes having an unknown biological function. Where the function of a gene or its product is unknown, genetic analysis in model organisms can be useful in placing such genes in known biochemical or genetic pathways. This is done by screening for extragenic mutations that either suppress or enhance the effect of mutations in the gene under analysis. For example, extragenic suppressors of loss-of-function mutations in a disease gene may turn on the affected genetic or biochemical pathway downstream of the mutant gene, while suppressors of gain-of-function mutations will probably turn the pathway off.

One model organism that can be used in the elucidation of the function of the presenilin genes is *C. elegans*, which contains three genes having homology to PS-1 and PS-2, with sel-12 having the highest degree of homology to the genes encoding the human presenilins. Sel-12 was discovered in a screen for genetic suppressers of an activated notch receptor, lin-12(d) (Levitan, D. et al., *Nature* 377: 351–354 (1995)). Lin-12 functions in development to pattern cell lineages. Hypermorphic mutations such as lin-12(d), which increase lin-12 activity, cause a "multi-vulval" phenotype, while hypomorphic mutations which decrease activity cause eversion of the vulva, as well as homeotic changes in several other cell lineages (Greenwald, I., et al., *Nature* 346: 197–199 (1990); Sundaram, M. et al., *Genetics* 135: 755–763 (1993)). Sel-12 mutations suppress hypermorphic lin-12(d) mutations, but only if the lin-12(d) mutations activate signaling by the intact lin-12(d) receptor (Levitan, D. et al., *Nature* 377: 351–354 (1995)). Lin-12 mutations that truncate the cytoplasmic domain of the receptor also activate signaling (Greenwald, I., et al., *Nature* 346: 197–199 (1990)), but are not suppressed by mutations of sel-12 (Levitan, D. et al., *Nature* 377: 351–354 (1995)). This implies that sel-12 mutations act upstream of the lin-12 signaling pathway, perhaps by decreasing the amount of functional lin-12 receptor present in the plasma membrane. In addition to suppressing certain lin-12 hypermorphic mutations, mutations to sel-12 cause a loss-of-function for egg laying, and thus internal accumulation of eggs, although the mutants otherwise appear anatomically normal (Levitan, D. et al., *Nature* 377: 351–354 (1995)). Sel-12 mutants can be rescued by either human PS-1 or PS-2, indicating that sel-12, PS-1 and PS-2 are functional homologues (Levitan, D., et al., *Proc. Natl. Acad. Sci. U.S.A* 93: 14940–14944 (1996)).

A second gene, sel-10, has been identified in a separate genetic screen for suppressors of lin-12 hypomorphic mutations. Loss-of-function mutations in sel-10 restore signaling by lin-12 hypomorphic mutants. As the lowering of sel-10 activity elevates lin-12 activity, it can be concluded that sel-10 acts as a negative regulator of lin-12 signaling. Sel-10 also acts as a negative regulator of sel-12, the *C. elegans* presenilin homologue (Levy-Lahad, E. et al., *Science* 269:973–977 (1995)). Loss of sel-10 activity suppresses the egg laying defect associated with hypomorphic mutations in sel-12 (Iva Greenwald, personal communication). The effect of loss-of-function mutations to sel-10 on lin-12 and sel-12 mutations indicates that sel-10 acts as a negative regulator of both lin-12/notch and presenilin activity. Thus, a human homologue of *C. elegans* sel-10 would be expected to interact genetically and/or physiologically with human presenilin genes in ways relevant to the pathogenesis of Alzheimer's Disease.

In view of the foregoing, it will be clear that there is a continuing need for the identification of genes related to AD, and for the development of assays for the identification of agents capable of interfering with the biological pathways that lead to AD.

INFORMATION DISCLOSURE

Hubbard E J A, Wu G, Kitajewski J, and Greenwald I (1997) Sel-10, a negative regulator of lin-12 activity in *Caenorhabditis elegans*, encodes a member of the CDC4 family of proteins. Genes & Dev 11:3182–3193.

Greenwald-I; Seydoux-G (1990) Analysis of gain-of-function mutations of the lin-12 gene of *Caenorhabditis elegans*. Nature. 346: 197–9

Kim T-W, Pettingell W H, Hallmark O G, Moir R D, Wasco W, Tanzi R (1997) Endoproteolytic cleavage and proteasomal degradation of presenilin 2 in transfected cells. J Biol Chem 272:11006–11010.

Levitan-D; Greenwald-I (1995) Facilitation of lin-12-mediated signalling by sel-12, a *Caenorhabditis elegans* S182 Alzheimer's disease gene. Nature. 377: 351–4.

Levitan-D; Doyle-T G; Brousseau-D; Lee-M K; Thinakaran-G; Slunt-H H; Sisodia-S S; Greenwald-I (1996) Assessment of normal and mutant human presenilin function in *Caenorhabditis elegans*. Proc. Natl. Acad. Sci. U.S.A. 93: 14940–4.

Sundaram-M; Greenwald-I (1993) Suppressors of a lin-12 hypomorph define genes that interact with both lin-12 and glp-1 in *Caenorhabditis elegans*. Genetics. 135: 765–83.

Sundaram-M; Greenwald-I (1993) Genetic and phenotypic studies of hypomorphic lin-12 mutants in *Caenorhabditis elegans*. Genetics. 135: 755–63.

F55B12.3 GenPep Report (WMBL locus CEF55B12, accession z79757).

WO 97/11956

SUMMARY OF THE INVENTION

The present invention provides isolated nucleic acid molecules comprising a polynucleotide encoding human sel-10, which is expressed in hippocampal cells and in mammary cells. Unless otherwise noted, any reference herein to sel-10 will be understood to refer to human sel-10, and to encompass both hippocampal and mammary sel-10. Fragments of hippocampal sel-10 and mammary sel-10 are also provided.

In a preferred embodiment, the invention provides an isolated nucleic acid molecule comprising a polynucleotide having a sequence at least 95% identical to a sequence selected from the group consisting of:

(a) a nucleotide sequence encoding a human sel-10 polypeptide having the complete amino acid sequence selected from the group consisting of SEQ ID NO:3, SEQ ID NO:4, SEQ ID NO:5, SEQ ID NO:6, and SEQ ID NO:7, or as encoded by the cDNA clone contained in ATCC Deposit No.98978;

(b) a nucleotide sequence encoding a human sel-10 polypeptide having the complete amino acid sequence selected from the group consisting of SEQ ID NO:8, SEQ ID NO:9, and SEQ ID NO: 10, or as encoded by the cDNA clone contained in ATCC Deposit No. 98979; and (c) a nucleotide sequence complementary to the nucleotide sequence of (a) or (b).

In another aspect, the invention provides an isolated nucleic acid molecule comprising a polynucleotide which hybridizes under stringent conditions to a polynucleotide encoding sel-10, or fragments thereof.

The present invention also provides vectors comprising the isolated nucleic acid molecules of the invention, host cells into which such vectors have been introduced, and recombinant methods of obtaining a sel-10 polypeptide comprising culturing the above-described host cell and isolating the sel-10 polypeptide.

In another aspect, the invention provides isolated sel-10 polypeptides, as well as fragments thereof. In a preferred embodiment, the sel-10 polypeptides have an amino acid sequence selected from the group consisting of SEQ ID NO:3, 4, 5, 6, 7, 8, 9, and 10. Isolated antibodies, both polyclonal and monoclonal, that bind specifically to sel-10 polypeptides are also provided.

BRIEF DESCRIPTION OF THE FIGURES

FIGS. 1A and 1B are western blots showing protein expression in HEK293 cells transfected with PS1-C-FLAG, 6-myc-N-sel-10, and APP695NL-KK cDNAs.

DETAILED DESCRIPTION OF THE INVENTION

Figure 1A:
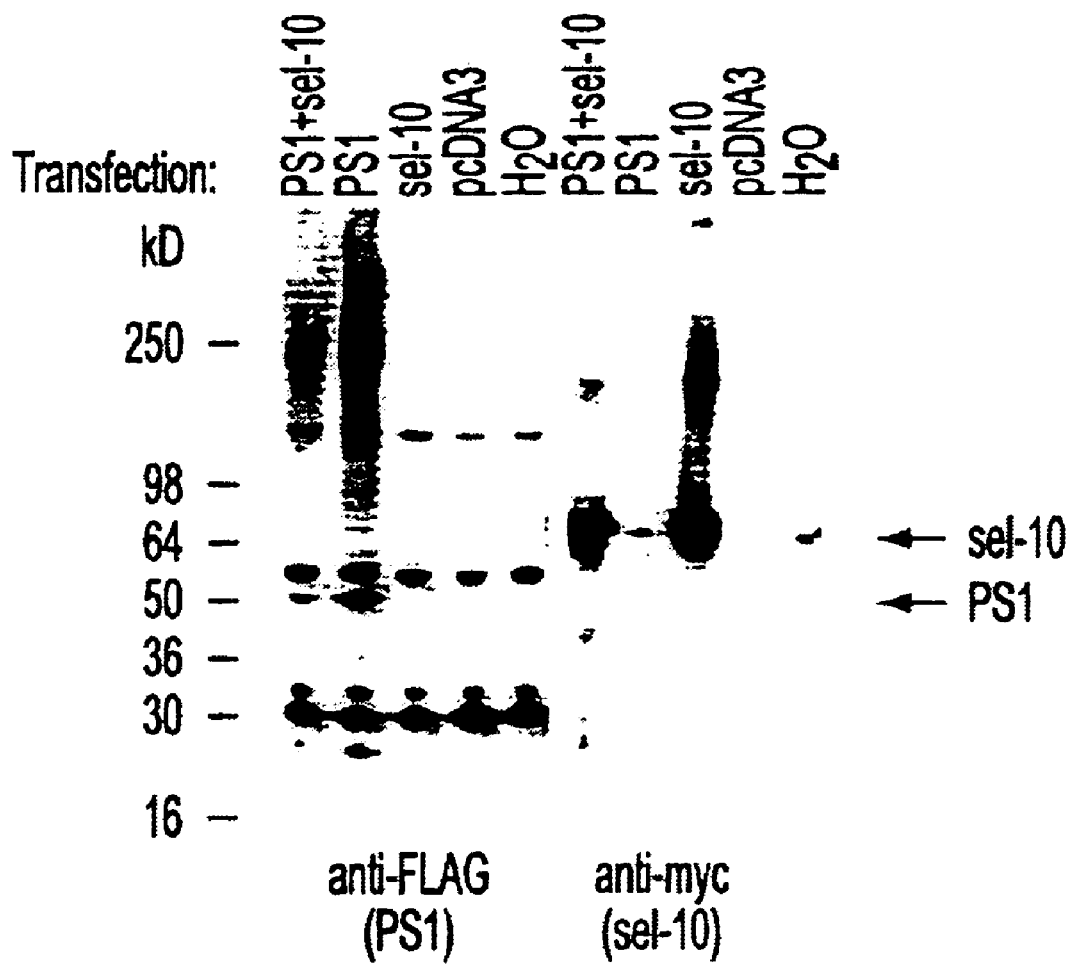
FIGS. 1A and 1B.

The present invention provides isolated nucleic acid molecules comprising a polynucleotide encoding human sel-10. The nucleotide sequence of human hippocampal sel-10 (hhsel-10), which sequence is given in SEQ ID NO:1, encodes five hhsel-10 polypeptides (hhsel-10-(1), hhsel-10-(2), hhsel-10-(3), hhsel-10-(4), and hhsel-10-(5), referred to collectively herein as hhsel-10). The nucleotide sequence of human mammary sel-10 (hmsel-10), which sequence is given in SEQ ID NO:2, encodes three hmsel-10 polypeptides (hmSel-10-(1), hmSel-10-(2), and hmsel-10-(3), referred to collectively herein as hmsel-10). The nucleotide sequences of the hhsel-10 polynucleotides are given in SEQ ID NO. 1, where nucleotide residues 45–1928 of SEQ ID NO. 1 correspond to hhsel-10-(1), nucleotide residues 150–1928 of SEQ ID NO. 1 correspond to hhSel-10-(2), nucleotide residues 267–1928 of SEQ ID NO. 1 correspond to hhSel-10-(3), nucleotide residues 291–1928 of SEQ ID NO. 1 correspond to hhSel-10-(4), and nucleotide residues 306–1928 of SEQ ID NO. 1 correspond to hhSel-10-(5). The nucleotide sequences of the hmSel-10 polynucleotides are given in SEQ ID NO. 2, where nucleotide residues 180–1949 of SEQ ID NO. 2 correspond to hmSel-10-(1), nucleotide residues 270–1949 of SEQ ID NO. 2 correspond to hmSel-10-(2), and nucleotide residues 327–1949 of SEQ ID NO. 2 correspond to hmSel-10-(3). The amino acid sequences of the polypeptides encoded by the hhSel-10 and hm-Sel-10 nucleic acid molecules are given as follows: SEQ ID NOS: 3, 4, 5, 6, and 7 correspond to the hhSel-10-(1), hhSel-10-(2), hhSel-10-(3). hhSel-10-(4), and hhSel-10-(5) polypeptides, respectively, and SEQ ID NOS: 8, 9, and 10 correspond to the hmSel-10-(1), hmSel-10-(2), and hmSel-10-(3) polypeptides, respectively. Unless otherwise noted, any reference herein to sel-10 will be understood to refer to human sel-10, and to encompass all of the hippocampal and mammary sel-10 nucleic acid molecules (in the case of reference to sel-10 nucleic acid, polynucleotide, DNA, RNA, or gene) or polypeptides (in the case of reference to sel-10 protein, polypeptide, amino acid sequnce). Fragments of hippocampal sel-10 and mammary sel-10 nucleic acid molecules and polypeptides are also provided.

The nucleotide sequence of SEQ ID NO: 1 was obtained as described in Example 1, and is contained in cDNA clone PNV 102-1, which was deposited on Nov. 9, 1998, in accordance with the Budapest Treaty at the American Type Culture Collection, 10801 University Blvd., Manassas, Va. 20110, and given accession number 98978. The nucleotide sequence of SEQ ID NO:2 was obtained as described in Example 1, and is contained in cDNA clone PNV 108-2, which was deposited on Nov. 9, 1998, in accordance with the Budapest Treaty at the American Type Culture Collection, 10801 University Blvd., Manassas, Va. 20110, and given accession number 98979.

The human sel-10 polypeptides of the invention share homology with *C. elegans* sel-10, as well as with members of the β-transducin protein family, including yeast CDC4, and human LIS-1. This family is characterized by the presence of an F-box and multiple WD-40 repeats (Li, J., et al., *Proc. Natl. Acad. Sci. U.S.A.* 92:12180–12184 (1995)). The repeats are 20–40 amino acids long and are bounded by gly-his (GH) and trp-asp (WD) residues. The three dimensional structure of β-transducin indicates that the WD40 repeats form the arms of a seven-bladed propeller like structure (Sondek, J., et al., *Nature* 379:369–374 (1996)). Each blade is formed by four alternating pleats of beta-sheet with a pair of the conserved aspartic acid residues in the protein motif forming the limits of one internal beta strand. WD40 repeats are found in over 27 different proteins which represent diverse functional classes (Neer, E. J., et al., *Nature* 371:297–300 (1994)). These regulate cellular functions including cell division, cell fate determination, gene transcription, signal transduction, protein degradation, mRNA modification and vesicle fusion. This diversity in function has led to the hypothesis that β-transducin family members provide a common scaffolding upon which multiprotein complexes can be assembled.

The nucleotide sequence given in SEQ ID NO: 1 corresponds to the nucleotide sequence encoding hhsel-10, while the nucleotide sequence given in SEQ ID NO:2 corresponds to the nucleotide sequence encoding hmsel-10. The isolation and sequencing of DNA encoding sel-10 is described below in Examples 1 and 2.

As is described in Examples 1 and 2, automated sequencing methods were used to obtain the nucleotide sequence of sel-10. The sel-10 nucleotide sequences of the present invention were obtained for both DNA strands, and are believed to be 100% accurate. However, as is known in the art, nucleotide sequence obtained by such automated methods may contain some errors. Nucleotide sequences determined by automation are typically at least about 90%, more typically at least about 95% to at least about 99.9% identical to the actual nucleotide sequence of a given nucleic acid molecule. The actual sequence may be more precisely determined using manual sequencing methods, which are well known in the art. An error in sequence which results in an insertion or deletion of one or more nucleotides may result in a frame shift in translation such that the predicted amino acid sequence will differ from that which would be predicted from the actual nucleotide sequence of the nucleic acid molecule, starting at the point of the mutation. The sel-10 DNA of the present invention includes cDNA, chemically synthesized DNA, DNA isolated by PCR, genomic DNA, and combinations thereof. Genomic sel-10 DNA may be obtained by screening a genomic library with the sel-10 cDNA described herein, using methods that are well known in the art. RNA transcribed from sel-10 DNA is also encompassed by the present invention.

Due to the degeneracy of the genetic code, two DNA sequences may differ and yet encode identical amino acid sequences. The present invention thus provides isolated nucleic acid molecules having a polynucleotide sequence encoding any of the sel-10 polypeptides of the invention, wherein said polynucleotide sequence encodes a sel-10 polypeptide having the complete amino acid sequence of SEQ ID NOs:3–10, or fragments thereof.

Also provided herein are purified sel-10 polypeptides, both recombinant and non-recombinant. Variants and derivatives of native sel-10 proteins that retain any of the biological activities of sel-10 are also within the scope of the present invention. As is described above, the sel-10 polypeptides of the present invention share homology with yeast CDC4. As CDC4 is known to catalyze ubiquitination of specific cellular proteins (Feldman et al., *Cell* 91:221 (1997)), it may be inferred that sel-10 will also have this activity. Assay procedures for demonstrating such activity are well known, and involve reconstitution of the ubiquitinating system using purified human sel-10 protein together with the yeast proteins Cdc4p, Cdc53p and Skp1p, or their human orthologs, and an E1 enzyme, the E2 enzyme Cdc34p or its human ortholog, ubiquitin, a target protein and an ATP regenerating system (Feldman et al., 1997). Skp1p associates with Cdc4p through a protein domain called an F-box (Bai et al., *Cell* 86:263 (1996)). The F-box protein motif is found in yeast CDC4, *C. elegans* sel-10, mouse sel-10 and human sel-10. The sel-10 ubiquitination system may be reconstituted with the *C. elegans* counterparts of the yeast components, e.g., cul-1 (also known as lin-19) protein substituting for Cdc53p (Kipreos et al., *Cell* 85:829 (1996)) and the protein F46A9 substituting for Skp1p, or with their mammalian counterparts, e.g., Cul-2 protein substituting for Cdc53p (Kipreos et al., 1996) and mammalian Skp1p substituting for yeast Skp1p. A phosphorylation system provided by a protein kinase is also included in the assay system as per Feldman et al., 1997.

Sel-10 variants may be obtained by mutation of native sel-10-encoding nucleotide sequences, for example. A sel-10 variant, as referred to herein, is a polypeptide substantially homologous to a native sel-10 but which has an amino acid sequence different from that of native sel-10 because of one or more deletions, insertions, or substitutions in the amino acid sequence. The variant amino acid or nucleotide sequence is preferably at least about 80% identical, more preferably at least about 90% identical, and most preferably at least about 95% identical, to a native sel-10 sequence. Thus, a variant nucleotide sequence which contains, for example, 5 point mutations for every one hundred nucleotides, as compared to a native sel-10 gene, will be 95% identical to the native protein. The percentage of sequence identity, also termed homology, between a native and a variant sel-10 sequence may also be determined, for example, by comparing the two sequences using any of the computer programs commonly employed for this purpose, such as the Gap program (Wisconsin Sequence Analysis Package, Version 8 for Unix, Genetics Computer Group, University Research Park, Madison Wis.), which uses the algorithm of Smith and Waterman (*Adv. Appl. Math.* 2: 482–489 (1981)).

Alterations of the native amino acid sequence may be accomplished by any of a number of known techniques. For example, mutations may be introduced at particular locations by procedures well known to the skilled artisan, such as oligonucleotide-directed mutagenesis, which is described by Walder et al. (*Gene* 42:133 (1986)); Bauer et al. (*Gene* 37:73 (1985)); Craik (*BioTechniques*, January 1985, pp. 12–19); Smith et al. (*Genetic Engineering: Principles and Methods*, Plenum Press (1981)); and U.S. Pat. Nos. 4,518,584 and 4,737,462.

Sel-10 variants within the scope of the invention may comprise conservatively substituted sequences, meaning that one or more amino acid residues of a sel-10 polypeptide are replaced by different residues that do not alter the secondary and/or tertiary structure of the sel-10 polypeptide. Such substitutions may include the replacement of an amino acid by a residue having similar physicochemical properties, such as substituting one aliphatic residue (Ile, Val, Leu or Ala) for another, or substitution between basic residues Lys and Arg, acidic residues Glu and Asp, amide residues Gln and Asn, hydroxyl residues Ser and Tyr, or aromatic residues Phe and Tyr. Further information regarding making phenotypically silent amino acid exchanges may be found in Bowie et al., *Science* 247:1306–1310 (1990). Other sel-10 variants which might retain substantially the biological activities of sel-10 are those where amino acid substitutions have been made in areas outside functional regions of the protein.

In another aspect, the invention provides an isolated nucleic acid molecule comprising a polynucleotide which hybridizes under stringent conditions to a portion of the nucleic acid molecules described above, e.g., to at least about 15 nucleotides, preferably to at least about 20 nucleotides, more preferably to at least about 30 nucleotides, and still more preferably to at least about from 30 to at least about 100 nucleotides, of one of the previously described nucleic acid molecules. Such portions of nucleic acid molecules having the described lengths refer to, e.g., at least about 15 contiguous nucleotides of the reference nucleic acid molecule. By stringent hybridization conditions is intended overnight incubation at about 42/C. for about 2.5 hours in 6×SSC/0.1% SDS, followed by washing of the filters in 1.0×SSC at 65/C., 0.1% SDS.

Fragments of the sel-10-encoding nucleic acid molecules described herein, as well as polynucleotides capable of hybridizing to such nucleic acid molecules may be used as a probe or as primers in a polymerase chain reaction (PCR). Such probes may be used, e.g., to detect the presence of sel-10 nucleic acids in in vitro assays, as well as in Southern and northern blots. Cell types expressing sel-10 may also be identified by the use of such probes. Such procedures are well known, and the skilled artisan will be able to choose a probe of a length suitable to the particular application. For PCR, 5' and 3' primers corresponding to the termini of a desired sel-10 nucleic acid molecule are employed to isolate and amplify that sequence using conventional techniques.

Other useful fragments of the sel-10 nucleic acid molecules are antisense or sense oligonucleotides comprising a single-stranded nucleic acid sequence capable of binding to a target sel-10 mRNA (using a sense strand), or sel-10 DNA (using an antisense strand) sequence.

In another aspect, the invention includes sel-10 polypeptides with or without associated native pattern glycosylation. Sel-10 expressed in yeast or mammalian expression systems (discussed below) may be similar to or significantly different from a native sel-10 polypeptide in molecular weight and glycosylation pattern. Expression of sel-10 in bacterial expression systems will provide non-glycosylated sel-10.

The polypeptides of the present invention are preferably provided in an isolated form, and preferably are substantially purified. Sel-10 polypeptides may be recovered and purified from recombinant cell cultures by well-known methods, including ammonium sulfate or ethanol precipitation, anion or cation exchange chromatography, phosphocellulose chromatography, hydrophobic interaction chromatography, affinity chromatography, hydroxylapatite chromatography and lectin chromatography. In a preferred embodiment, high performance liquid chromatography (HPLC) is employed for purification.

The present invention also relates to vectors comprising the polynucleotide molecules of the invention, as well as host cell transformed with such vectors. Any of the polynucleotide molecules of the invention may be joined to a vector, which generally includes a selectable marker and an origin of replication, for propagation in a host. Because the invention also provides sel-10 polypeptides expressed from the polynucleotide molecules described above, vectors for the expression of sel-10 are preferred. The vectors include DNA encoding any of the sel-10 polypeptides described above or below, operably linked to suitable transcriptional or translational regulatory sequences, such as those derived from a mammalian, microbial, viral, or insect gene. Examples of regulatory sequences include transcriptional promoters, operators, or enhancers, mRNA ribosomal binding sites, and appropriate sequences which control transcription and translation. Nucleotide sequences are operably linked when the regulatory sequence functionally relates to the DNA encoding sel-10. Thus, a promoter nucleotide sequence is operably linked to a sel-10 DNA sequence if the promoter nucleotide sequence directs the transcription of the sel-10 sequence.

Selection of suitable vectors to be used for the cloning of polynucleotide molecules encoding sel-10, or for the expression of sel-10 polypeptides, will of course depend upon the host cell in which the vector will be transformed, and, where applicable, the host cell from which the sel-10 polypeptide is to be expressed. Suitable host cells for expression of sel-10 polypeptides include prokaryotes, yeast, and higher eukaryotic cells, each of which is discussed below.

The sel-10 polypeptides to be expressed in such host cells may also be fusion proteins which include regions from heterologous proteins. Such regions may be included to allow, e.g., secretion, improved stability, or facilitated purification of the polypeptide. For example, a sequence encoding an appropriate signal peptide can be incorporated into expression vectors. A DNA sequence for a signal peptide (secretory leader) may be fused in-frame to the sel-10 sequence so that sel-10 is translated as a fusion protein comprising the signal peptide. A signal peptide that is functional in the intended host cell promotes extracellular secretion of the sel-10 polypeptide. Preferably, the signal sequence will be cleaved from the sel-10 polypeptide upon secretion of sel-10 from the cell. Non-limiting examples of signal sequences that can be used in practicing the invention include the yeast I-factor and the honeybee melatin leader in sf9 insect cells.

In a preferred embodiment, the sel-10 polypeptide will be a fusion protein which includes a heterologous region used to facilitate purification of the polypeptide. Many of the available peptides used for such a function allow selective binding of the fusion protein to a binding partner. For example, the sel-10 polypeptide may be modified to comprise a peptide to form a fusion protein which specifically binds to a binding partner, or peptide tag. Non-limiting examples of such peptide tags include the 6-His tag, thioredoxin tag, FLAG tag, hemaglutinin tag, GST tag, and OmpA signal sequence tag. As will be understood by one of skill in the art, the binding partner which recognizes and binds to the peptide may be any molecule or compound including metal ions (e.g., metal affinity columns), antibodies, or fragments thereof, and any protein or peptide which binds the peptide. These tags may be recognized by fluorescein or rhodamine labeled antibodies that react specifically with each type of tag Suitable host cells for expression of sel-10 polypeptides include prokaryotes, yeast, and higher eukaryotic cells. Suitable prokaryotic hosts to be used for the expression of sel-10 include bacteria of the genera Escherichia, Bacillus, and Salmonella, as well as members of the genera Pseudomonas, Streptomyces, and Staphylococcus. For expression in, e.g., *E. coli*, a sel-10 polypeptide may include an N-terminal methionine residue to facilitate expression of the recombinant polypeptide in a prokaryotic host. The N-terminal Met may optionally then be cleaved from the expressed sel-10 polypeptide.

Expression vectors for use in prokaryotic hosts generally comprise one or more phenotypic selectable marker genes. Such genes generally encode, e.g., a protein that confers antibiotic resistance or that supplies an auxotrophic requirement. A wide variety of such vectors are readily available from commercial sources. Examples include pSPORT vectors, pGEM vectors (Promega), pPROEX vectors (LTI, Bethesda, Md.), Bluescript vectors (Stratagene), and pQE vectors (Qiagen).

Sel-10 may also be expressed in yeast host cells from genera including Saccharomyces, Pichia, and Kluveromyces. Preferred yeast hosts are *S. cerevisiae* and *P. pastoris*. Yeast vectors will often contain an origin of replication sequence from a 2T yeast plasmid, an autonomously replicating sequence (ARS), a promoter region, sequences for polyadenylation, sequences for transcription termination, and a selectable marker gene.

Vectors replicable in both yeast and *E. coli* (termed shuttle vectors) may also be used. In addition to the above-mentioned features of yeast vectors, a shuttle vector will also include sequences for replication and selection in *E. coli*. Direct secretion of sel-10 polypeptides expressed in yeast hosts may be accomplished by the inclusion of nucleotide sequence encoding the yeast I-factor leader sequence at the 5' end of the sel-10-encoding nucleotide sequence.

Insect host cell culture systems may also be used for the expression of Sel-10 polypeptides. In a preferred embodiment, the sel-10 polypeptides of the invention are expressed using a baculovirus expression system. Further information regarding the use of baculovirus systems for the expression of heterologous proteins in insect cells are reviewed by Luckow and Summers, *Bio/Technology* 6:47 (1988).

In another preferred embodiment, the sel-10 polypeptide is expressed in mammalian host cells. Non-limiting examples of suitable mammalian cell lines include the COS-7 line of monkey kidney cells (Gluzman et al., *Cell* 23:175 (1981)) and Chinese hamster ovary (CHO) cells.

The choice of a suitable expression vector for expression of the sel-10 polypeptides of the invention will of course depend upon the specific mammalian host cell to be used, and is within the skill of the ordinary artisan. Examples of suitable expression vectors include pcDNA3 (Invitrogen) and pSVL (Pharmacia Biotech). Expression vectors for use in mammalian host cells may include transcriptional and translational control sequences derived from viral genomes. Commonly used promoter sequences and enhancer sequences which may be used in the present invention include, but are not limited to, those derived from human cytomegalovirus (CMV), Adenovirus 2, Polyoma virus, and Simian virus 40 (SV40). Methods for the construction of mammalian expression vectors are disclosed, for example, in Okayama and Berg (*Mol. Cell. Biol.* 3:280 (1983)); Cosman et al. (*Mol. Immunol.* 23:935 (1986)); Cosman et al. (*Nature* 312:768 (1984)); EP-A-0367566; and WO 91/18982.

The polypeptides of the present invention may also be used to raise polyclonal and monoclonal antibodies, which are useful in diagnostic assays for detecting sel-10 polypeptide expression. Such antibodies may be prepared by conventional techniques. See, for example, *Antibodies: A Laboratory Manual*, Harlow and Land (eds.), Cold Spring Harbor Laboratory Press, Cold Spring Harbor, N.Y., (1988); *Monoclonal Antibodies, Hybridomas: A New Dimension in Biological Analyses*, Kennet et al. (eds.), Plenum Press, New York (1980).

The sel-10 nucleic acid molecules of the present invention are also valuable for chromosome identification, as they can hybridize with a specific location on a human chromosome. There is a current need for identifying particular sites on the chromosome, as few chromosome marking reagents based on actual sequence data (repeat polymorphisms) are presently available for marking chromosomal location. Once a sequence has been mapped to a precise chromosomal location, the physical position of the sequence on the chromosome can be correlated with genetic map data. The relationship between genes and diseases that have been mapped to the same chromosomal region can then be identified through linkage analysis, wherein the coinheritance of physically adjacent genes is determined. Whether a gene appearing to be related to a particular disease is in fact the cause of the disease can then be determined by comparing the nucleic acid sequence between affected and unaffected individuals.

The sel-10 polypeptides of the invention, and the DNA encoding them, may also be used to further elucidate the biological mechanism of AD, and may ultimately lead to the identification of compounds that can be used to alter such mechanisms. The sel-10 polypeptides of the invention are 47.6% identical and 56.7% similar to *C. elegans* sel-10. As is described above, mutations to *C. elegans* sel-10 are known to suppress mutations to sel-12 that result in a loss-of-function for egg laying, and also to suppress certain hypomorphic mutations to lin-12. Mutations to *C. elegans* sel-12 can also be rescued by either of the human AD-linked genes PS-1 (42.7% identical to sel-12) or PS-2 (43.4% identical to sel-12). However, human PS-1 with a familial AD-linked mutant has a reduced ability to rescue sel-12 mutants (Levitan, D. et al., *Proc. Natl. Acad. Sci. USA* 93: 14940–14944 (1996)).

This demonstrated interchangeability of human and *C. elegans* genes in the notch signaling pathway makes it reasonable to predict that mutations of human sel-10 will suppress mutations to PS-1 or PS-2 that lead to AD, especially in light of the predicted structure of sel-10. As described above, PS-1 and PS-2 mutations that lead to AD are those which interfere with the proteolytic processing of PS-1 or PS-2. The sel-10 polypeptides of the invention are members of the β-transducin protein family, which includes yeast CDC4, a component of an enzyme which functions in the ubiquitin-dependent protein degradation pathway. Thus, human sel-10 may regulate presenilin degradation via the ubiquitin-proteasome pathway. Alternatively, or in addition, human sel-10 may alter presenilin function by targeting for degradation through ubiquitination a modulator of presenilin activity, e.g., a negative regulator. Therefore, mutations to sel-10 may reverse the faulty proteolytic processing of PS-1 or PS-2 which occurs as a result of mutation to PS-1 or PS-2 or otherwise increase presenilin function. For the same reason, inhibition of sel-10 activity may also act to reverse PS-1 or PS-2 mutations. Thus, it may be hypothesized that compounds which inhibit either the expression or the activity of the human sel-10 polypeptides of the invention may reverse the effects of mutations to PS-1 or PS-2, and thus be useful for the prevention or treatment of AD.

Thus, C. elegans may be used as a genetic system for the identification of agents capable of inhibiting the activity or expression of the human sel-10 polypeptides of the invention. A suitable C. elegans strain for use in such assays lacks a gene encoding active C. elegans sel-10, and exhibits a loss-of-function for egg-laying resulting from an inactivated sel-12 gene. Construction of C. elegans strains having a loss-of-function for egg-laying due to mutation of sel-12 may be accomplished using routine methods, as both the sequence of sel-12 (Genebank accession number U35660) and mutations to sel-12 resulting in a loss-of-function for egg laying are known (see Levitan et al., *Nature* 377: 351–354 (1995), which describes construction of C. elegans sel-12(ar171)). An example of how to make such a strain is also given in Levitan et al. (*Nature* 377: 351–354 (1995)). Wild-type C. elegans sel-10 in the C. elegans sel-12(ar171)), is also mutagenized using routine methods, such as the technique used for sel-12 mutagenesis in Levitan et al., supra.

In order to identify compounds inhibiting human sel-10 activity, a DNA vector containing a human sel-10 gene encoding any of the wild-type human sel-10 proteins of the invention is introduced into the above-described C. elegans strain. In a preferred embodiment, the heterologous human sel-10 gene is integrated into the C. elegans genome. The gene is then expressed, using techniques described in Levitan et al. (*Proc. Natl. Acad. Sci. USA* 93: 14940–14944 (1996)). Test compounds are then administered to this strain in order to determine whether a given agent is capable of inhibiting sel-10 activity so as to suppress mutations to sel-12 or lin-12 that result in egg-laying defects. Egg-laying in this strain is then determined, e.g. by the assay described in Levitan et al. (*Proc. Natl. Acad. Sci. USA* 93: 14940–14944 (1996)). To confirm that the compound's effect on egg-laying is due to inhibition of sel-10 activity, the action of the compound can be tested in a second biochemical or genetic pathway that is known to be affected by loss-of-function mutations in sel-10 (e.g., further elevation of lin-12 activity in lin-12(d) hypomorphic strains). Such assays may be performed as described in Sundarem and Greenwald (*Genetics* 135: 765–783 (1993)).

Alternatively, compounds are tested for their ability to inhibit the E3 Ubiquitin Ligating Enzyme. Assays procedures for demonstrating such activity are well known, and involve reconstitution of the ubiquitinating system using purified human sel-10 protein together with the yeast proteins Cdc4p, Cdc53p and Skp1p and an E1 enzyme, the E2 enzyme Cdc34p, ubiquitin, a target protein and an ATP regenerating system (Feldman et al., 1997). The sel-10 ubiquitination system may also be reconstituted with the C. elegans counterparts of the yeast components, e.g., cul-1 (also known as lin-19) protein substituting for Cdc53p (Kipreos et al., *Cell* 85:829 (1996)) and the protein F46A9 substituting for Skp1p, or with their mammalian counterparts, e.g., Cul-2 protein substituting for Cdc53p (Kipreos et al., ibid.) and mammalian Skp1p substituting for yeast Skp1p. A phosphorylation system provided by a protein kinase is also to be included in the assay system as per Feldman et al., 1997.

Alternatively, cell lines which express human sel-10 due to transformation with a human sel-10 cDNA and which as a consequence have elevated APP processing and formation of $A\beta_{1-40}$ or $A\beta_{1-42}$ may also be used for such assays as in Example 3. Compounds may be tested for their ability to reduce the elevated $A\beta$ processing seen in the sel-10 transformed cell line.

Compounds that rescue the egg-laying defect or that inhibit E3 Ubiquitin Ligating Enzyme are then screened for their ability to cause a reduction in the production of A-beta$_{1-40}$ or A-beta$_{1-42}$ in a human cell line. Test compounds are used to expose IMR-32 or other human cell lines known to produce A-beta$_{1-40}$ or A-beta$_{1-42}$ (Asami-Okada et al., *Biochemistry* 34: 10272–10278 (1995)), or in human cell lines engineered to express human APP at high levels. In these assays, A-beta$_{1-40}$ or A-beta$_{1-42}$ is measured in cell extracts or after release into the medium by ELISA or other assays which are known in the art (Borchelt et al., *Neuron* 17: 1005–1013 (1996); Citron et al., *Nat. Med.* 3: 67–72 (1997)).

Having generally described the invention, the same will be more readily understood by reference to the following examples, which are provided by way of illustration and are not intended as limiting.

EXAMPLES

Example 1

Identification of a Human Homologue to C. elegans Sel-10

Results

Identification of sel-10 in ACEDB: Sel-10 maps between the cloned polymorphisms arP3 and TCPARI just to the left of him-5 [ACEDB entry wm95p536]. Three phage lambda clones have been sequenced across the interval, F53C11, F09F3, and F55B12. Sel-10 is reported to have homology to yeast cdc4 [ACEDB entry wm97ab259]. Blast search revealed a single ORF with homology to yeast cdc4 (CC4_YST) within the interval defined by arP3 and TCPARI corresponding to the GenPep entry F55B12.3. F55B12.3, like yeast cdc4, is a member of the β-transducin protein family. This family is characterized by the presence of multiple WD40 repeats [Neer, E. J. et al., *Nature* 371: 297–300 (1994)].

Identification of a human sel-10 homologue, Incyte 028971: The GenPep entry F55B12.3 was used to search the LifeSeq, LifeSeq FL and EMBL data bases using tblastn. The search revealed multiple homologies to β-transducin family members including LIS-1 (S36113 and P43035), a gene implicated in Miller-Dieker lissencephaly, a *Xenopus laevis* gene, TRCPXEN (U63921), and a human contig in LifeSeq FL, 028971. Since there also are multiple β-transducin family members within the C. elegans genome, these were collected using multiple blast searches and then clustered with the sel-10 candidate genes. Multiple alignments were performed with the DNAStar program Megalign using the Clustal method. This revealed that LIS-1 clustered with T03F6.F, a different β-transducin family member and thus excluded it as a candidate sel-10 homologue. TRCPXEN clustered with K10B2.1, a gene which also clusters with F55B12.3 and CC4YST, while Incyte 028971 clustered with sel-10. Thus, Incyte 028971 appears to encode the human homologue of C. elegans sel-10. Sequence homology between sel-10 and 028971 is strongest in the region of the protein containing 7 repeats of the WD40 motif. The Incyte 028971 contig contains 44 ESTs from multiple libraries including pancreas, lung, T-lymphocytes, fibroblasts, breast, hippocampus, cardiac muscle, colon, and others.

Public EST: Blastx searches with the DNA sequence 028971 against the TREMBLP dataset identified a single homologous mouse EST (W85144) from the IMAGE Library, Soares mouse embryo NbME13.5–14.5. The blastx alignment of 028971 with W85144 and then with F55B12.3 revealed a change in reading frame in 028971 which probably is due to a sequencing error.

Blastn searches of the EMBL EST database with the 028971 DNA sequence revealed in addition to W85144, three human EST that align with the coding sequence of 028971 and six EST that align with the 3' untranslated region of the 028971 sequence.

Protein Motifs: Two protein motifs were identified in F55B12.3 which are shared with yeast cdc4, mouse w85144 and human 028971. These are an F-box in the N-terminal domain and seven β-transducin repeats in the C-terminal domain.

Discussion

The sel-10 gene encodes a member of the β-transducin protein family. These are characterized by the presence of multiple WD40 repeats [Neer, E. J. et al., Nature 371: 297–300 (1994)]. The repeats are 20–40 amino acids long and are bounded by gly-his (GH) and trp-asp (WD) residues. Solution of the three dimensional structure of β-transducin indicates that the WD40 repeats form the arms of a seven-bladed propeller like structure [Sondek, J. et al., Nature 379: 369–74 (1996)]. Each blade is formed by four alternating pleats of beta-sheet with a pair of the conserved aspartic acid residues in the protein motif forming the limits of one internal beta strand. WD40 repeats are found in over 27 different proteins which represent diverse functional classes [Neer, E. J. et al., Nature 371: 297–300 (1994)]. These regulate cellular functions including cell division, cell fate determination, gene transcription, signal transduction, protein degradation, mRNA modification and vesicle fusion. This diversity in function has led to the hypothesis that β-transducin family members provide a common scaffolding upon which multiprotein complexes can be assembled.

The homology of sel-10, 28971 and W85144 to the yeast cdc4 gene suggests a functional role in the ubiquitin-proteasome pathway for intracellular degradation of protein. Mutations of the yeast cdc4 gene cause cell cycle arrest by blocking degradation of Sic1, an inhibitor of S-phase cyclin/cdk complexes [King, R. W. et al., Science 274: 1652–9 (1996)]. Phosphorylation of Sic1 targets it for destruction through the ubiquitin-proteasome pathway. This pathway consists of three linked enzyme reactions that are catalyzed by multiprotein complexes [Ciechanover, A., Cell 79: 13–21 (1994); Ciechanover, A. and A. L. Schwartz, FASEB J. 8: 182–91 (1994)]. Initially, the C-terminal glycine of ubiquitin is activated by ATP to form a high energy thiol ester intermediate in a reaction catalyzed by the ubiquitin-activating enzyme, E1. Following activation, an E2 enzyme (ubiquitin conjugating enzyme) transfers ubiquitin from E1 to the protein target. In some cases, E2 acts alone. In others, it acts in concert with an E3 ubiquitin-ligating enzyme which binds the protein substrate and recruits an E2 to catalyze ubiquitination. E2 ubiquitin-conjugating enzymes comprise a fairly conserved gene family, while E3 enzymes are divergent in sequence [Ciechanover, A., Cell 79: 13–21 (1994); Ciechanover, A. and A. L. Schwartz, FASEB J. 8: 182–91 (1994)].

In yeast, mutation of the E2 ubiquitin-conjugating enzyme, cdc34, causes cell cycle arrest through failure to degrade the Sic1 inhibitor of the S-phase cyclin/cdk complex [King, R. W. et al., Science 274: 1652–9 (1996)]. Sic1 normally is degraded as cells enter the G1-S phase transition, but in the absence of cdc34, Sic1 escapes degradation and its accumulation causes cell cycle arrest. Besides cdc34, cdc4 is one of three other proteins required for the G1-S phase transition. The other two are cdc53 and Skp1. As discussed above, cdc4 contains two structural motifs, seven WD40 repeats (which suggests that the protein forms a beta-propeller) and a structural motif shared with cyclin F which is an interaction domain for Skp1 [Bai, C. et al., Cell 86: 263–74 (1996)]. Insect cell lysates containing cdc53, cdc4 and skp1 (and also ubiquitin, cdc34 and E1) can transfer ubiquitin to Sic1 suggesting that one or more of these components functions as an E3 ubiquitin-ligating enzyme [King, R. W. et al., Science 274: 1652–9 (1996)]. Increased expression of either cdc4 or Skp1 partially rescues loss of the other.

In C. elegans, mutation of sel-10 has no visible phenotype indicating that sel-10 does not play a role in regulation of the cell-cycle. A closely related, C. elegans β-transducin family member, K10B2.6 may play that role as it clusters with the gene TRCP_XEN from Xenopus laevis which rescues yeast cell cycle mutants arrested in late anaphase due to a failure to degrade cyclin B [Spevak, W. et al., Mol. Cell. Biol. 13: 4953–66 (1993)]. If sel-10 does encode a component of an E3-ubiquitin ligating enzyme, how might it suppress sel-12 and enhance lin-12 mutations? The simplest hypothesis is that sel-10 regulates degradation of both proteins via the ubiquitin-proteasome pathway. Both sel-12 and lin-12 are transmembrane proteins. Sel-12 crosses the membrane 8 times such that its N- and C-termini face the cytosol [Kim, T. W. et al., J. Biol. Chem. 272: 11006–10 (1997)], while lin-12 is a type 1 transmembrane protein (Greenwald, I. and G. Seydoux, Nature 346: 197–9 (1990)). Both are ubiquitinated, and in the case of human PS2, steady state levels increase in cells treated with an inhibitor of the proteasome, N-acetyl-L-leucinal-L-norleucinal and lactacystin (Li, X. and I. Greenwald, Neuron. 17: 1015–21 (1996)). Alternatively, sel-10 may target for degradation of a negative regulator of presenilin function.

The genetic analysis and protein function suggested by homology to cdc4 implies that drug inhibitors of human sel-10 may increase steady state levels of human presenilins. This could potentiate activity of the presenilin pathway and provide a means for therapeutic intervention in Alzheimer's disease.

Example 2

5'RACE Cloning of a Human cDNA Encoding Sel-10, an Extragenic Suppressor of Presenilin Mutations in C. elegans Materials and Methods Oligonucleotide primers for the amplification of the sel-10 coding sequence from C. elegans cDNA were prepared based on the sequence of F55B12.3, identified in Example 1 as the coding sequence for C. elegans sel-10. The primers prepared were: 5'-CGGGATCCACCATGGATGATGGAT CGATGACACC-3' (SEQ ID NO: 11) and 5'-GGAATT CCTTAAGGGTATACAGCATCAAAGTCG-3' (SEQ ID NO: 12). C. elegans mRNA was converted to cDNA using a BRL Superscript II Preamplification kit. The PCR product was digested with restriction enzymes BamHI and EcoRI (LTI, Gaithersberg, Md.) and cloned into pcDNA3.1 (Invitrogen). Two isolates were sequenced (ABI, Perkin-Elmer Corp).

The sequence of Incyte clone 028971 (encoding a portion of the human homologue of C. elegans sel-10), was used to design four antisense oligonucleotide primers: 5'-TCACTTCATGTCCACATCAAAGTCC-3' (SEQ ID NO: 13), 5'-GGTAATTACAAGTTCTTGTTGAACTG (SEQ ID NO: 14), 5'-CCCTGCAACGTGTGTAGACAG G-3' (SEQ ID NO: 15), and 5'-CCAGTCTCTGCATTCCAC ACTTTG-3' (SEQ ID NO:16) to amplify the missing 5' end of human sel-10. The Incyte LifeSeq "Electronic Northern"

analysis was used to identify tissues in which sel-10 was expressed. Two of these, hippocampus and mammary gland, were chosen for 5' RACE cloning using a CloneTech Marathon kit and prepared Marathon-ready cDNA from hippocampus and mammary gland. PCR products were cloned into the TA vector pCR3.1 (Invitrogen), and isolates were sequenced. An alternate 5' oligonucleotide primer was also designed based on Incyte clones which have 5' ends that differ from the hippocampal sel-10 sequence: 5'-CTCAGACAGGTCAGGACATTTGG-3' (SEQ ID NO:17).

Blastn was used to search Incyte databases LifeSeq and LifeSeqFL. Gap alignments and translations were performed with GCG programs (Wisconsin Sequence Analysis Package, Version 8 for Unix, Genetics Computer Group, University Research Park, Madison Wis.).

Results

The coding sequence of the *C. elegans* sel-10: The predicted coding sequence of the *C. elegans* sel-10, F55B12.3, had originally been determined at the Genome Sequencing Center, Washington University, St. Louis, by using the computer program GeneFinder to predict introns and exons in the genomic cosmid F55B12. The hypothetical cDNA sequence was confirmed by amplifying this region from *C. elegans* cDNA, cloning, and sequencing it.

The coding sequence of the human sel-10 gene homologue: All of the 028971 antisense oligonucleotides amplified a 5' RACE product from human hippocampal and mammary cDNA. The longest PCR product from the hippocampal reactions was cloned and sequenced. This PCR reaction was designed to generate products which end at the predicted stop codon. Two isolates contained identical sequence which begins 880 bases before the beginning of the 028971 sequence. This sequence was confirmed by comparison with spanning Incyte cDNA clones. The Incyte clones that spanned the 5' end of the human sel-10 homologue were not annotated as F55B12.3, as the homology in this region between the human and *C. elegans* genes is low, and as the overlap between these clones and the annotated clones happened to be too small for them to be clustered in the Incyte database or uncovered by our blasting the Incyte database with the 028971 sequence.

The predicted protein sequences of human sel-10 have 47.6% identity and 56.7% similarity to *C. elegans* sel-10. The N-terminus of the human sel-10 sequence begins with 4 in-frame methionines. In addition to the WD40 repeats described above, the human sequence also contains a region homologous to the CDC4 F-box for binding Skp1, as expected for a sel-10 homologue.

Different human sel-10 mRNAs expressed in mammary and hippocampal tissues:

Several additional human sel-10 ESTs which differ from the hippocampal sequence were identified. These are an exact match, which indicates that the alternative transcript is probably real. Comparison of these sequences with the human hippocampal sel-10 sequence shows divergence prior to the 4th in-frame methionine and then exact sequence match thereafter. An oligonucleotide primer specific for the 5' end of this alternative transcript was found to amplify a product from mammary but not hippocampal cDNA. This indicates either that the human sel-10 transcript undergoes differential splicing in a tissue-specific fashion or that the gene contains multiple, tissue specific promoters.

Discussion

5'RACE and PCR amplification were used to clone a full-length cDNA encoding the human homologue of the *C. elegans* gene, sel-10. Sequence analysis confirms the earlier prediction that sel-10 is a member of the CDC4 family of proteins containing F-Box and WD40 Repeat domains. Two variants of the human sel-10 cDNA were cloned from hippocampus and mammary gland which differed in 5' sequence preceding the apparent site of translation initiation. This implies that the gene may have two or more start sites for transcription initiation which are tissue-specific or that the pattern of exon splicing is tissue-specific.

Example 3

Expression of Epitope-Tagged Sel-10 in Human Cells, and Perturbation of Amyloid β Peptide Processing by Human Sel-10

Materials and Methods

Construction of Epitope-Tagged Sel-10: Subcloning, Cell Growth and Transfection:

An EcoR1 site was introduced in-frame into the human sel-10 cDNA using a polymerase chain reaction (PCR) primed with the oligonucleotides 237 (5'-GGAATTCCAT GAAAAGATTGGACCATGGTTCTG-3') (SEQ ID NO: 18) and 206 (5'-GGAATTCCTCACTTCATGT-CACATCAAAGTCCAG-3') (SEQ ID NO:19). The resulting PCR product was cloned into the EcoR1 site of the vector pCS2+MT. This fused a 5' 6-myc epitope tag in-frame to the fifth methionine of the hippocampal sel-10 cDNA, i.e., upstream of nucleotide 306 of the sequence given in SEQ ID NO:1. The nucleotide sequence of this construct, designated 6myc-N-sel-10, is given in SEQ ID NO: 20, while the amino acid sequence of the polypeptide encoded thereby is given in SEQ ID NO: 21. The hippocampal and mammary sel-10 cDNA diverge upstream of this methionine. A PS1 cDNA with a 3 -FLAG tag (PS1-C-FLAG) was subcloned into the pcDNA3.1 vector. An APP cDNA containing the Swedish NL mutation and an attenuated ER retention sequence consisting of the addition of a di-lysyl motif to the C-terminus of APP695 (APP695NL-KK) was cloned into vector pIRES-EGFP (Mullan et al., Nat Genet 1992 Aug;1(5):345–7). HEK293 and IMR32 cells were grown to 80% confluence in DMEM with 10% FBS and transfected with the above cDNA. A total of 10 mg total DNA/6×10$^6$ cells was used for transfection with a single plasmid. For cotransfections of multiple plasnids, an equal amount of each plasmid was used for a total of 10 mg DNA using LipofectAmine (BRL).

In order to construct C-term V5 his tagged sel-10 and the C-term mychis tagged sel-10, the coding sequence of human hippocampal sel-10 was amplified using oligonucleotides primers containing a KpnI restriction site on the 5' primer: 5'-GGGTACCCCTCATTATTCCCTCGAGTTCTTC-3' (SEQ ID NO:22) and an EcoRI site on the 3' primer: 5'-GGAATTCCTTCATGTCCACATCAAAGTCC-3' (SEQ ID NO:23), using the original human sel-10 RACE pcr product as template. The product was digested with both KpnI and EcoRI and cloned into either the vector pcDNA6/V5-His A or pcDNA3.1/Myc-His(+) A (Invitrogen). The nucleotide sequence of independent isolates was confirmed by dideoxy sequencing. The nucleotide sequence of the C-term V5 his tagged sel-10 is given in SEQ ID NO: 24, while the amino acid sequence of the polypeptide encoded thereby is given in SEQ ID NO: 25. The nucleotide sequence of independent isolates was confirmed by dideoxy sequencing. The nucleotide sequence of the C-term mychis tagged sel-10 is given in SEQ ID NO: 26, while the amino acid sequence of the polypeptide encoded thereby is given in SEQ ID NO: 27.

Clonal Selection of transformed cells by FACS: Cell samples were analyzed on an EPICS Elite ESP flow cytometer (Coulter, Hialeah, Fla.) equipped with a 488 nm excitation line supplied by an air-cooled argon laser. EGFP emission was measured through a 525 nm band-pass filter and fluorescence intensity was displayed on a 4-decade log scale after gating on viable cells as determined by forward and right angle light scatter. Single green cells were separated into each well of one 96 well plate containing growth medium without G418. After a four day recovery period, G418 was added to the medium to a final concentration of 400 mg/ml. Wells with clones were expanded from the 96 well plate to a 24 well plate and then to a 6 well plate with the fastest growing colonies chosen for expansion at each passage.

Immunofluorescence: Cells grown on slides were fixed 48 hrs after transfection with 4% formaldehyde and 0.1% Triton X-100 in PBS for 30 min on ice and blocked with 10% Goat serum in PBS (blocking solution) 1 hr RT (i.e., 25° C.), followed by incubation with mouse anti-myc (10 mg/ml) or rabbit anti-FLAG (0.5 mg/ml) antibody 4° C. O/N and then fluorescein-labeled goat anti-mouse or anti-rabbit antibody (5 mg/ml) in blocking solution 1 hr at 25° C.

Western blotting: Cell lysates were made 48 hrs after transfection by incubating $10^5$ cells with 100 ml TENT (50 mM Tris-HCl pH 8.0, 2 mM EDTA, 150 mM NaCl, 1% Triton X-100, 1× protease inhibitor cocktail) 10 min on ice followed by centrifugation at 14,000 g. The supernatant was loaded on 4–12% NuPage gels (50 mg protein/lane) and electrophoresis and transfer were conducted using an Xcell II Mini-Cell system (Novex). The blot was blocked with 5% milk in PBS 1 hr RT and incubated with anti-myc or anti-FLAG antibody (described in "Immunofluorescence" above) 4° C. O/N, then sheep anti-mouse or anti-rabbit antibody-HRP (0.1 mg/ml) 1 hr RT, followed by Supersignal (Pierce) detection.

ELISA: Cell culture supernatant or cell lysates (100 ml formic acid/$10^6$ cells) were assayed in the following double antibody sandwich ELISA, which is capable of detecting levels of $A\beta_{1-40}$ and $A\beta_{1-42}$ peptide in culture supernatant.

Human Aβ 1–40 or 1–42 was measured using monoclonal antibody (mAb) 6E10 (Senetek, St. Louis, Mo.) and biotinylated rabbit antiserum 162 or 164 (NYS Institute for Basic Research, Staten Island, N.Y.) in a double antibody sandwich ELISA. The capture antibody 6E10 is specific to an epitope present on the N-terminal amino acid residues 1–16 of hAβ. The conjugated detecting antibodies 162 and 164 are specific for hAβ 1–40 and 1–42, respectively. The sandwich ELISA was performed according to the method of Pirttila et al. (*Neurobiology of Aging* 18: 121–7 (1997)). Briefly, a Nunc Maxisorp 96 well immunoplate was coated with 100 μl/well of mAb 6E10 (5 μg/ml) diluted in 0.1M carbonate-bicarbonate buffer, pH 9.6 and incubated at 4° C. overnight. After washing the plate 3× with 0.01M DPBS (Modified Dulbecco's Phosphate Buffered Saline (0.008M sodium phosphate, 0.002M potassium phosphate, 0.14M sodium chloride, 0.01 M potassium chloride, pH 7.4) from Pierce, Rockford, Ill.) containing 0.05% of Tween-20 (DPBST), the plate was blocked for 60 min with 200 μl of 10% normal sheep serum (Sigma) in 0.01M DPBS to avoid non-specific binding. Human Aβ 1–40 or 1–42 standards 100 μl/well (Bachem, Torrance, Calif.) diluted, from a 1 mg/ml stock solution in DMSO, in non transfected conditioned cell medium was added after washing the plate, as well as 100 μl/well of sample i.e. filtered conditioned medium of transfected cells. The plate was incubated for 2 hours at room temperature and 4° C. overnight. The next day, after washing the plate, 100 μl/well biotinylated rabbit antiserum 162 1:400 or 164 1:50 diluted in DPBST+0.5% BSA was added and incubated at room temperature for 1 hr 15 min. Following washes, 100 μl/well neutravidin-horseradish peroxidase (Pierce, Rockford, Ill.) diluted 1:10,000 in DPBST was applied and incubated for 1 hr at room temperature. After the last washes 100 μl/well of o-phenylnediamine dihydrochloride (Sigma Chemicals, St. Louis, Mo.) in 50 mM citric acid/100 mM sodium phosphate buffer (Sigma Chemicals, St. Louis, Mo.), pH 5.0, was added as substrate and the color development was monitored at 450 nm in a kinetic microplate reader for 20 min. using Soft max Pro software.

Results

Transfection of HEK293 cells: Transfection efficiency was monitored through the use of vectors that express green fluorescent protein (GFP) or by immunofluorescent detection of epitope-tagged sel-10 or PS1. An N-terminal 6-myc epitope was used to tag human sel-10 (6myc-N-sel-10), while PS1 was tagged with a C-terminal FLAG epitope (PS1-C-FLAG). APP695 was modified by inclusion of the Swedish NL mutation to increase Aβ processing and an attenuated endoplasmic reticulum (ER) retention signal consisting of a C-terminal di-lysine motif (APP695NL-KK). The di-lysine motif increases Aβ processing about two fold. The APP695NL-KK construct was inserted into the first cistron of a bicistronic vector containing GFP (pIRES-EGFP, Invitrogen) to allow us to monitor transfection efficiency. Transfection efficiency in HEK293 cells was about 50% for transfections with a single plasmid DNA. For cotransfections with two plasmids, about 30–40% of the cells expressed both proteins as detected by double immunofluorescence.

Figure 1B:
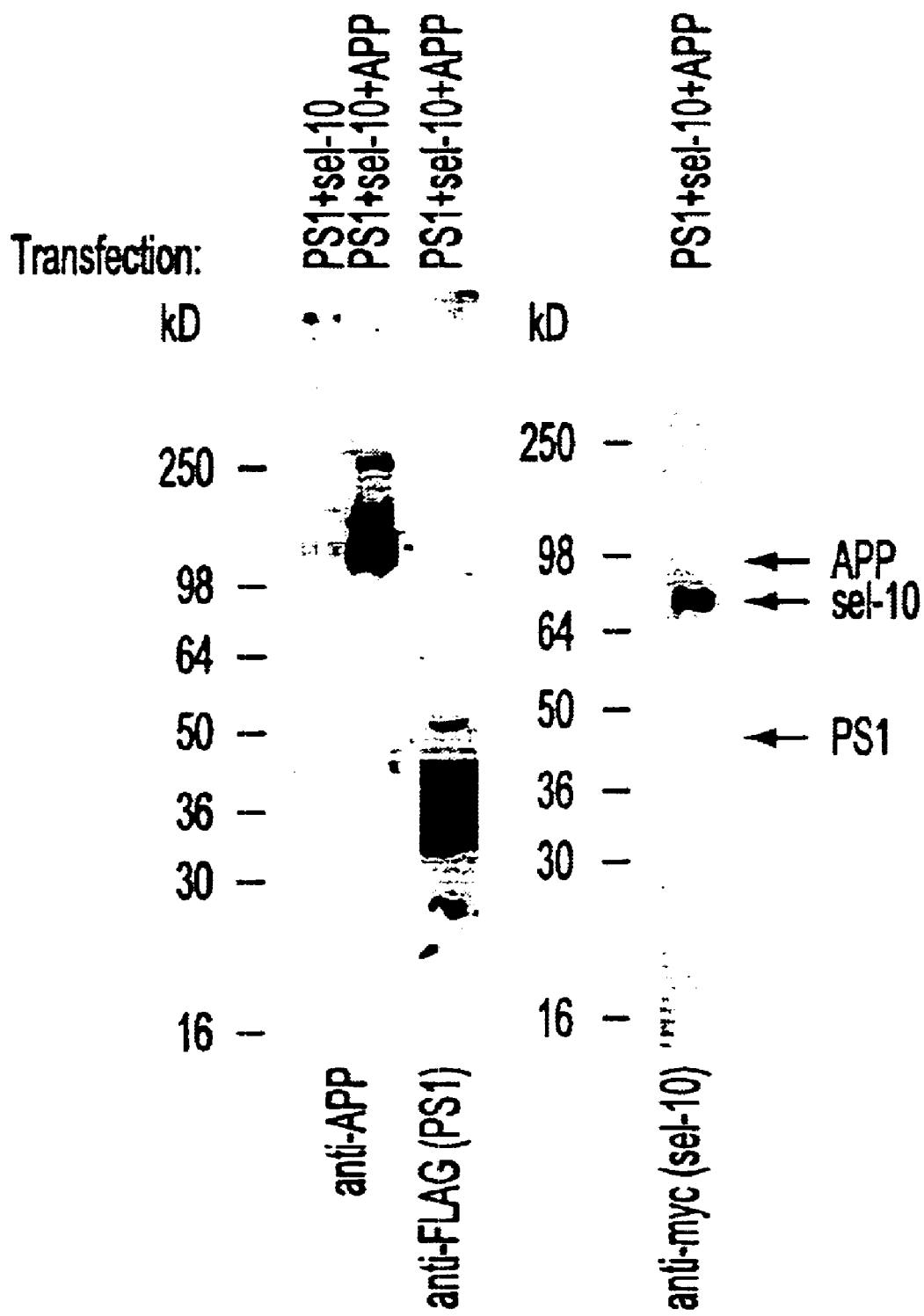

Expression of recombinant protein in transfected HEK293 cells was confirmed by Western blot as illustrated for PS1-C-FLAG and 6myc-N-sel-10 (FIG. 1A). In the case of cotransfections with three plasmids (PS1-C-FLAG+ 6myc-N-sel-10+APP), all three proteins were detected in the same cell lysate by Western blot (FIG. 1B) using appropriate antibodies.

Effect of 6myc-N-sel-10 and PS1-C-FLAG on Aβ processing: Cotransfection of APP695NL-KK with 6myc-N-sel-10 or PS1-C-FLAG into HEK293 cells increased the release of Ab1–40 and Ab1–42 peptide into the culture supernatant by 2- to 3-fold over transfections with just APP695NL-KK (Table 1). Cotransfection of APP695NL-KK with both 6myc-N-sel-10 and PS1-C-FLAG increased Ab release still further (i.e., 4- to 6-fold increase). In contrast, the ratio of Ab1–42/(Ab1–40+Ab1–42) released into the supernatant decreased about 50%. The subtle decrease in the ratio of Ab1–42/(Ab1–40+Ab1–42) reflects the larger increase in Ab 1–40 relative to Ab 1–42. Neither 6myc-N-sel-10 nor PS1-C-FLAG affected endogenous Ab production in HEK293 cells. Similar observations were also obtained in IMR32 cells (Table 2). However, IMR32 cells transfected less well than HEK293 cells, so the stimulation of APP695NL-KK processing by cotransfection with 6myc-N-sel-10 or PS1-C-FLAG was lower.

Levels of Ab 1–40 expressed in HEK293 cells transfected with APP695NL-KK were sufficient to measure Ab peptide in both the culture supernatant and cell pellet. Considerably more Ab 1–40 is detected in the HEK293 cell pellet than in the supernatant in cells transfected with just APP695NL-KK. Cotransfection with 6myc-N-sel-10 or PS1-C-FLAG proportionately decreased Ab 1–40 in the cell pellet and increased Ab in the culture supernatant. This implies that 6myc-N-sel-10 and PS1-C-FLAG alter processing or trafficking of APP such that proportionately more Ab is released from the cell.

Effect of 6myc-N-sel-10 and PS1-C-FLAG expression on endogenous Aβ processing: The effect of 6myc-N-sel-10 on the processing of endogenous APP by human cells was assessed by creating stably transformed HEK293 cell lines expressing these proteins. Two cell lines expressing 6myc-N-sel-10 were derived (sel-10/2 & sel-10/6) as well as a control cell line transformed with pcDNA3.1 vector DNA. Both 6myc-N-sel-10 cell lines expressed the protein as shown by Western blot analysis. Endogenous production of Ab 1–40 was increased in both 6myc-N-sel-10 cell lines in contrast to vector DNA transformed cells Table 3). In addition, stable expression of 6myc-N-sel-10 significantly increased Ab production after transfection with APP695NL-KK plasmid DNA (Table 3). Similar results were obtained with 6 stable cell lines expressing PS1-C-FLAG. All 6 cell lines showed significant elevation of endogenous Aβ processing and all also showed enhanced processing of Ab after transfection with APP695NL-KK (Table 3). In addition, the increase of Aβ processing seen with 6myc-N-sel-10 was also seen with sel-10 tagged at the C-terminus with either mychis or v5his (See Table 4). Both C-terminal and N-terminal tags resulted in an increase in Aβ processing.

Discussion

These data suggest that, when over expressed, 6myc-N-sel-10 as well as PS1-C-FLAG alter Aβ processing in both transient and stable expression systems. A 6-myc epitope tag was used in these experiments to allow detection of sel-10 protein expression by Western blot analysis. If as its sequence homology to yeast CDC4 suggests, sel-10 is an E2-E3 ubiquitin ligase, it should be possible to identify the proteins it targets for ubiquitination. Since the presenilins are degraded via the ubiquitin-proteasome pathway, PS1 & PS2 are logical targets of sel-10 catalyzed ubiquitination [Kim et al., *J. Biol. Chem.* 272:11006–11010 (1997)]. How sel-10 affects Aβ processing is not understood at this point. In the future, it will be necessary to determine if sel-10 & PS1 increase Aβ processing by altering production, processing, transport, or turn-over of APP, and whether the effect of PS1 is mediated or regulated by sel-10.

These experiments suggest that sel-10 is a potential drug target for decreasing Ab levels in the treatment of AD. They also show that *C. elegans* is an excellent model system in which to investigate presenilin biology in the context of AD. Thus, as is shown by cotransfection experiments, as well as in stable transformants, expression of 6myc-N-sel10 or PS1-C-FLAG increases Aβ processing. An increase in Aβ processing was seen in both HEK293 cells and IMR32 cells after cotransfection of 6myc-N-sel10 or PS1-C-FLAG with APP695NL-KK. In stable transformants of HEK293 cells expressing 6myc-Sel10 or PS1-C-FLAG, an increase in endogenous Aβ processing was observed, as well as an increase in Aβ processing after transfection with APP695NL-KK. This suggests that inhibitors of either sel-10 and/or PS1, may decrease Aβ processing, and could have therappeutic potential for Alzheimer's disease.

It will be clear that the invention may be practiced otherwise than as particularly described in the foregoing description and examples.

Numerous modifications and variations of the present invention are possible in light of the above teachings and, therefore, are within the scope of the invention.

The entire disclosure of all publications cited herein are hereby incorporated by reference.

TABLE 1

Effect of 6myc-N-sel-10 and PS1-C-FLAG transient transfection on Ab levels in HEK293 cell supernatants.

| Plasmids Transfected | Ab1-42 ng/ml | Ab1-40 ng/ml | Ab1-42/total Ab ng/ml |
|---|---|---|---|
| pcDNA3 | 81 ± 20 | 231 ± 50 | 0.26 ± 0.05 |
| 6myc-N-sel-10 | 67 ± 7 | 246 ± 34 | 0.21 ± 0.03 |
| PS1-C-FLAG | 75 ± 18 | 227 ± 45 | 0.25 ± 0.03 |
| PS1-C-FLAG + 6myc-N-sel-10 | 77 ± 21 | 220 ± 26 | 0.25 ± 0.03 |
| APP695NL-KK | 141 ± 27 | 896 ± 103 | 0.14 ± 0.02 |
| APP695NL-KK + 6myc-N-sel-10 | 308 ± 17 | 2576 ± 190 | 0.11 ± 0.00 |
| APP695NL-KK + PS1-C-FLAG | 364 ± 39 | 3334 ± 337 | 0.09 ± 0.00 |
| APP695NL-KK + PS1-C-FLAG + 6myc-N-sel-10 | 550 ± 20 | 5897 ± 388 | 0.09 ± 0.00 |

TABLE 2

Effect of 6myc-N-sel-10 and PS1-C-FLAG transient transfection on Ab levels in IMR32 cell supernatants.

| Plasmids Transfected | Ab1-42 ng/ml | Ab1-40 ng/ml | Ab1-42/total Ab ng/ml |
|---|---|---|---|
| pcDNA3 | 65 ± 3 | 319 ± 146 | 0.19 ± 0.06 |
| 6myc-N-sel-10 | 63 ± 0 | 246 ± 53 | 0.21 ± 0.04 |
| PS1-C-FLAG | 67 ± 6 | 307 ± 79 | 0.18 ± 0.04 |
| PS1-C-FLAG + 6myc-N-sel-10 | 67 ± 6 | 302 ± 94 | 0.20 ± 0.08 |
| APP695NL-KK | 66 ± 5 | 348 ± 110 | 0.17 ± 0.05 |
| APP695NL-KK + 6myc-N-sel-10 | 75 ± 18 | 448 ± 141 | 0.15 ± 0.03 |
| APP695NL-KK + PS1-C-FLAG | 63 ± 26 | 466 ± 72 | 0.12 ± 0.02 |
| APP695NL-KK + PS1-C-FLAG + 6myc-N-sel-10 | 81 ± 26 | 565 ± 179 | 0.12 ± 0.01 |

TABLE 3

Endogenous and exogenous Ab1-40 and Ab1-42 levels in supernatants from stable transformants of HEK293 cells.

| | GFP Transfection | | APP695NL-KK Transfection | |
|---|---|---|---|---|
| Stable Line | Ab1-40 ng/ml | Ab1-42 ng/ml | Ab1-40 ng/ml | Ab1-42 ng/ml |
| 6myc-N-sel10/2 | 297 ± 29 | 109 ± 17 | 4877 ± 547 | 750 ± 32 |
| 6myc-N-sel10/6 | 168 ± 18 | 85 ± 11 | 8310 ± 308 | 1391 ± 19 |
| PS1-C-FLAG/2 | 97 ± 6 | 68 ± 8 | 3348 ± 68 | 493 ± 21 |
| PS1-C-FLAG/8 | 118 ± 11 | 85 ± 17 | 3516 ± 364 | 515 ± 36 |
| PS1-C-FLAG/9 | 83 ± 20 | 67 ± 16 | 2369 ± 73 | 350 ± 12 |
| PS1-C-FLAG/11 | 152 ± 17 | 68 ± 13 | 4771 ± 325 | 599 ± 25 |
| PS1-C-FLAG/12 | 141 ± 12 | 50 ± 10 | 4095 ± 210 | 449 ± 21 |
| PS1-C-FLAG/13 | 270 ± 139 | 61 ± 28 | 6983 ± 304 | 745 ± 41 |
| pcDNA3/1 | 43 ± 13 | 75 ± 15 | 1960 ± 234 | 61 ± 6 |

TABLE 4

Sel-10 constructs with epitope tags at the N or C terminus increase Aβ 1–40 and Aβ 1–42.

| construct | Aβ 1–40 | % increase | P-value | Aβ 1–42 | % increase | P-value |
|---|---|---|---|---|---|---|
| pcDNA | 4240 ± 102 | | | 614 ± 10 | | |
| 6myc-N-sel-10 | 7631 ± 465 | 80% | $3.7 \times 10^{-6}$ | 1136 ± 73 | 46% | $7.9 \times 10^{-6}$ |
| sel-10-C-mychis | 5485 ± 329 | 29% | $1.8 \times 10^{-4}$ | 795 ± 50 | 29% | $4.0 \times 10^{-4}$ |
| sel-10-C-V5his | 6210 ± 498 | 46% | $1.2 \times 10^{-4}$ | 906 ± 73 | 48% | $2.1 \times 10^{-4}$ |

What is claimed is:

1. An isolated double or single stranded nucleic acid molecule wherein said nucleic acid molecule encodes a human sel-10 polypeptide comprising the amino acid sequence of SEQ ID NO:7.

2. The nucleic acid molecule of claim 1, wherein said nucleic acid molecule comprises the nucleotide sequence of residues 306–1928 of SEQ ID NO:1.

3. The nucleic acid molecule of claim 1, wherein said nucleic acid encodes a human sel-10 polypeptide comprising the amino acid sequence of SEQ ID NO:3.

4. The nucleic acid molecule of claim 3, wherein said nucleic acid molecule comprises the nucleotide sequence of residues 45–1928 of SEQ ID NO:1.

5. The nucleic acid molecule of claim 1, wherein said nucleic acid encodes a human sel-10 polypeptide comprising the amino acid sequence of SEQ ID NO:4.

6. The nucleic acid molecule of claim 5, wherein said nucleic acid molecule comprises the nucleotide sequence of residues 150–1928 of SEQ ID NO:1.

7. The nucleic acid molecule of claim 1, wherein said nucleic acid encodes a human sel-10 polypeptide comprising the amino acid sequence of SEQ ID NO:5.

8. The nucleic acid molecule of claim 7, wherein said nucleic acid molecule comprises the nucleotide sequence of residues 267–1928 of SEQ ID NO:1.

9. The nucleic acid molecule of claim 1, wherein said nucleic acid encodes a human sel-10 polypeptide comprising the amino acid sequence of SEQ ID NO:6.

10. The nucleic acid molecule of claim 9, wherein said nucleic acid molecule comprises the nucleotide sequence of residues 291–1928 of SEQ ID NO:1.

11. The nucleic acid molecule of claim 1, wherein said nucleic acid encodes a human sel-10 polypeptide comprising the amino acid sequence of SEQ ID NO:8.

12. The nucleic acid molecule of claim 11, wherein said nucleic acid molecule comprises the nucleotide sequence of residues 180–1949 of SEQ ID NO:2.

13. The nucleic acid molecule of claim 1, wherein said nucleic acid encodes a human sel-10 polypeptide comprising the amino acid sequence of SEQ ID NO:9.

14. The nucleic acid molecule of claim 13, wherein said nucleic acid molecule comprises the nucleotide sequence of residues 270–1949 of SEQ ID NO:2.

15. The nucleic acid molecule of claim 1, wherein said nucleic acid encodes a human sel-10 polypeptide comprising the amino acid sequence of SEQ ID NO:21.

16. The nucleic acid molecule of claim 15, wherein said nucleic acid molecule comprises the nucleotide sequence of residues 1–1881 of SEQ ID NO:20.

17. The nucleic acid molecule of claim 1, wherein said nucleic acid encodes a human sel-10 polypeptide comprising the amino acid sequence of SEQ ID NO:25.

18. The nucleic acid molecule of claim 17, wherein said nucleic acid molecule comprises the nucleotide sequence of residues 1–2010 of SEQ ID NO:24.

19. The nucleic acid molecule of claim 1, wherein said nucleic acid encodes a human sel-10 polypeptide comprising the amino acid sequence of SEQ ID NO:27.

20. The nucleic acid molecule of claim 19, wherein said nucleic acid molecule comprises the nucleotide sequence of residues 1–2001 of SEQ ID NO:26.

21. A vector comprising the isolated nucleic acid molecule of claim 1.

22. The vector of claim 21 wherein the nucleic acid molecule is operably linked to a promoter for the expression of a sel-10 polypeptide.

23. A host cell comprising the vector of claim 22.

24. The host cell of claim 23, wherein said host is a eukaryotic host.

25. A method of obtaining a sel-10 polypeptide comprising culturing the host cell of claim 23 and isolating said sel-10 polypeptide.

26. An isolated nucleic acid molecule which is the complement of the nucleic acid molecule of claim 1.

27. A vector comprising the isolated nucleic acid molecule of claim 3.

28. The vector of claim 27 wherein the nucleic acid molecule is operably linked to a promoter for the expression of a sel-10 polypeptide.

29. A host cell comprising the vector of claim 28.

30. The host cell of claim 29, wherein said host is a eukaryotic host.

31. A method of obtaining a sel-10 polypeptide comprising culturing the host cell of claim 29 and isolating said sel-10 polypeptide.

32. An isolated nucleic acid molecule which is the complement of the nucleic acid molecule of claim 3.

33. A vector comprising the isolated nucleic acid molecule of claim 5.

34. The vector of claim 33, wherein the nucleic acid molecule is operably linked to a promoter for the expression of a sel-10 polypeptide.

35. A host cell comprising the vector of claim 34.

36. The host cell of claim 35, wherein said host is a eukaryotic host.

37. A method of obtaining a sel-10 polypeptide comprising culturing the host cell of claim 35 and isolating said sel-10 polypeptide.

38. An isolated nucleic acid molecule which is the complement to the nucleic acid molecule of claim 5.

39. A vector comprising the isolated nucleic acid molecule of claim 7.

40. The vector of claim 39, wherein the nucleic acid molecule is operably linked to a promoter for the expression of a sel-10 polypeptide.

41. A host cell comprising the vector of claim 40.

42. The host cell of claim 41, wherein said host is a eukaryotic host.

43. A method of obtaining a sel-10 polypeptide comprising culturing the host cell of claim 42 and isolating said sel-10 polypeptide.

44. A isolated nucleic acid molecule which is the complement to the nucleic acid molecule of claim 7.

45. A vector comprising the isolated nucleic acid molecule of claim 9.

46. The vector of claim 45 wherein the nucleic acid molecule is operably linked to a promoter for the expression of a sel-10 polypeptide.

47. A host cell comprising the vector of claim 46.

48. The host cell of claim 47, wherein said host is a eukaryotic host.

49. A method of obtaining a sel-10 polypeptide comprising culturing the host cell of claim 47 and isolating said sel-10 polypeptide.

50. An isolated nucleic acid molecule which is the complement to the nucleic acid molecule of claim 9.

51. A vector comprising the isolated nucleic acid molecule of claim 11.

52. The vector of claim 51 wherein the nucleic acid molecule is operably linked to a promoter for the expression of a sel-10 polypeptide.

53. A host cell comprising the vector of claim 52.

54. The host cell of claim 53, wherein said host is a eukaryotic host.

55. A method of obtaining a sel-10 polypeptide comprising culturing the host cell of claim 53 and isolating said sel-10 polypeptide.

56. An isolated nucleic acid molecule which is the complement to the nucleic acid molecule of claim 11.

57. A vector comprising the isolated nucleic acid molecule of claim 13.

58. The vector of claim 57 wherein the nucleic acid molecule is operably linked to a promoter for the expression of a sel-10 polypeptide.

59. A host cell comprising the vector of claim 58.

60. The host cell of claim 59 herein said host is a eukaryotic host.

61. A method of obtaining a sel-10 polypeptide comprising culturing the host cell of claim 59 and isolating said sel-10 polypeptide.

62. An isolated nucleic acid molecule which is the complement to the nucleic acid molecule of claim 13.

63. A vector comprising the isolated nucleic acid molecule of claim 15.

64. The vector of claim 63 wherein the nucleic acid molecule is operably linked to a promoter for the expression of a sel-10 polypeptide.

65. A host cell comprising the vector of claim 64.

66. The host cell of claim 65, wherein said host is a eukaryotic host.

67. A method of obtaining a sel-10 polypeptide comprising culturing the host cell of claim 66 and isolating said sel-10 polypeptide.

68. An isolated nucleic acid molecule which is the complement to the nucleic acid molecule of claim 15.

69. A vector comprising the isolated nucleic acid molecule of claim 17.

70. The vector of claim 69, wherein the nucleic acid molecule is operably linked to a promoter for the expression of a sel-10 polypeptide.

71. A host cell comprising the vector of claim 70.

72. The host cell of claim 71, wherein said host is a eukaryotic host.

73. A method of obtaining a sel-10 polypeptide comprising culturing the host cell of claim 28 and isolating said sel-10 polypeptide.

74. An isolated nucleic acid molecule which is the complement to the nucleic acid molecule of claim 17.

75. A vector comprising the isolated nucleic acid molecule of claim 19.

76. The vector of claim 75 wherein the nucleic acid molecule is operably linked to a promoter for the expression of a sel-10 polypeptide.

77. A host cell comprising the vector of claim 76.

78. The host cell of claim 77, wherein said host is a eukaryotic host.

79. A method of obtaining a sel-10 polypeptide comprising culturing the host cell of claim 77 and isolating said sel-10 polypeptide.

80. An isolated nucleic acid molecule which is the complement to the nucleic acid molecule of claim 19.

* * * * *

(12) EX PARTE REEXAMINATION CERTIFICATE (5373rd)

United States Patent
Gurney et al.

(10) Number: US 6,638,731 C1
(45) Certificate Issued: May 16, 2006

(54) HUMAN SEL-10 POLYPEPTIDES AND POLYNUCLEOTIDES THAT ENCODE THEM

(75) Inventors: Mark E. Gurney, Grand Rapids, MI (US); Adele M. Pauley, Plainwell, MI (US); Jinhe Li, Kalamazoo, MI (US)

(73) Assignee: Pharmacia & Upjohn Company, Kalamazoo, MI (US)

Reexamination Request:
No. 90/007,179, Aug. 23, 2004

Reexamination Certificate for:
Patent No.: 6,638,731
Issued: Oct. 28, 2003
Appl. No.: 09/213,888
Filed: Dec. 17, 1998

Related U.S. Application Data

(60) Provisional application No. 60/068,243, filed on Dec. 19, 1997.

(51) Int. Cl.
*C12P 21/06* (2006.01)
*C12N 1/20* (2006.01)
*C12N 15/00* (2006.01)
*C07H 21/04* (2006.01)

(52) U.S. Cl. ............... 435/69.1; 435/252.3; 435/320.1; 536/23.1

(58) Field of Classification Search ...................... None
See application file for complete search history.

(56) References Cited

U.S. PATENT DOCUMENTS 6,087,153 A * 7/2000 Greenwald et al. ..... 435/252.33

FOREIGN PATENT DOCUMENTS

| WO | WO 99/05307 | 2/1999 |
| WO | WO 99/32623 | 7/1999 |
| WO | WO 00/31263 | 6/2000 |

OTHER PUBLICATIONS

Wu, Guangyu, et al., "Evidence for functional and physical association between *Caenorhabditis elegans* SEL–10, a Cdc4p–related protein, and SEL–12 presenilin", Proc. Natl. Sci. USA, Dec. 1998, vol. 95, pp. 15787–15791.

* cited by examiner

*Primary Examiner*—Robert A. Wax

(57) ABSTRACT

The present invention provides isolated nucleic acid molecules comprising a polynucleotide encoding either of two alternative splice variants of human sel-10, one of which is expressed in hippocampal cells, and one of which is expressed in mammary cells. The invention also provides isolated sel-10 polypeptides and cell lines which express them in which $A\beta$ processing is altered.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–80 is confirmed.

* * * * *